US009023648B2

(12) United States Patent
Stevenson et al.

(10) Patent No.: US 9,023,648 B2
(45) Date of Patent: May 5, 2015

(54) METHOD OF TRANSDUCING NON-DIVIDING MYELOID CELLS UTILIZING CHIMERIC MURINE LEUKEMIA VIRUSES CONTAINING VPX

(75) Inventors: Mario Stevenson, Coconut Grove, FL (US); Rajnish Kaushik, Grafton, MA (US); Xiaonan Zhu, Worcester, MA (US)

(73) Assignee: University of Massachusetts, Boston, MA (US)

( * ) Notice: Subject to any disclaimer, the term of this patent is extended or adjusted under 35 U.S.C. 154(b) by 742 days.

(21) Appl. No.: 12/980,938

(22) Filed: Dec. 29, 2010

(65) Prior Publication Data
US 2011/0165683 A1    Jul. 7, 2011

Related U.S. Application Data

(60) Provisional application No. 61/284,996, filed on Dec. 30, 2009.

(51) Int. Cl.
*C12N 15/00* (2006.01)
*C12N 15/86* (2006.01)
*A61K 39/12* (2006.01)
*A61K 39/21* (2006.01)
*C07K 14/005* (2006.01)
*C12N 7/00* (2006.01)
*A61K 48/00* (2006.01)

(52) U.S. Cl.
CPC ............... *C12N 15/86* (2013.01); *A61K 48/00* (2013.01); *C07K 14/005* (2013.01); *C12N 7/00* (2013.01); *C12N 2740/13043* (2013.01); *C12N 2740/13045* (2013.01); *C12N 2740/13052* (2013.01); *C12N 2740/15022* (2013.01); *C12N 2740/15033* (2013.01); *C12N 2740/16043* (2013.01); *C12N 2740/16045* (2013.01); *C12N 2740/16052* (2013.01)

(58) Field of Classification Search
CPC ............... C12N 15/86; C12N 7/00; C12N 2740/13043; C12N 2740/16043; C07K 14/005
See application file for complete search history.

(56) References Cited

PUBLICATIONS

Kaushik, R., et al., Jul. 2009, A cellular restriction dictates the permissivity of nondividing monocytes/macrophages to lentivirus and gammaretrovirus infection, Cell Host & Microbe, 6:68-80.*
Kaushik, R., et al., 2009, A cellular restriction dictates the permissivity of nondividing monocytes/macrophages to lentivirus and gammaretrovirus infection, Cell Host & Microbe, 6:68-80.*
Yamashita, M., et al., 2009, Cellular restriction targeting viral capsids perturbs human immunodeficiency virus type 1 infection of nondividing cells, J. Virol. 83(19):9835-9843.*

Hrecka, K., et al., 2011, Vpx relieves inhibition of HIV-1 infection of macrophages mediated by the SAMHD1 protein, Nature 474:658-661.*
16th Conference on Retroviruses and Opportunistic Infections, Feb. 2009, San Francisco CA, Abstract 25: Kaushik, R., et al., "A Cellular Restriction Dictates the Cell Cycle-Dependence of Retrovirus Infection" ; Abstract 238: Zhu, X., et al., "Vpx Renders Monocytes Permissive to HIV-1 Infection by Counteracting a Restriction Factor"; poster: Zhu, X., et al., "Vpx Renders Monocytes Permissive to HIV-1 Infection by Counteracting a Restriction Factor".
Accola, M.A., et al. "A Conserved Dileucine-Containing Motif in p6*gag* Governs the Particle Association of Vpx and Vpr in Simian Immunodeficiency Virus $SIV_{mac}$ and $SIV_{agm}$", *Journal of Virology*, 73(12): 9992-9999 (1999).
Arthur, L.O., et al.,"Cellular Proteins Bound to Immunodeficiency Viruses: Implications for Pathogenesis and Vaccines", *Science*, 258: 1935-1938 (1992).
Ballict, J.W., et al., "Distinct Effects in Primary Macrophages and Lymphocytes of the Human Immunodeficiency Virus Type 1 Accessory Genes vpr, vpu and nef: Mutational Analysis of a Primary HIV-1 Isolate", *Virology*, 200: 623-631 (1994).
Bieniasz, P.D., et al., "Cell Cycle Dependence of Foamy Retrovirus Infection", Journal of *Virology*, 69(11): 7295-7299 (1995).
Bouyac-Bertoia, M., et al., "HIV-1 Infection Requires a Functional Integrase NLS", *Mol. Cell.*, 7: 1025-1035 (2001).
Bowerman, B., et al., "A Nucleoprotein Complex Mediates the Integration of Retroviral DNA", *Genes and Development*, 3: 469-478 (1989).
Bukrinsky, M.I., et al., "Active Nuclear Import of Human Immunodeficiency Virus Type 1 Preintegration Complexes", *Proc. Natl. Acad. Sci.*, 89: 6580-6584 (1992).
Bukrinsky, M.I., et al., "A Nuclear Localization Signal Within HIV-1 Matrix Protein that Governs Infection of Non-Dividing Cells", *Nature*, 365: 666-669 (1993).
Chiu, Y.L., et al., "Cellular APOBEC3G Restricts HIV-1 Infection in Resting CD4[+] T Cells", *Nature*, 435: 108-114 (2005).
Collman, R., et al., "Infection of Monocyte-Derived Macrophages with Human Immunodeficiency Virus Type 1 (HIV-1)-Monocyte-tropic and Lymphocute-tropic Strains of HIV-1 Show Distinctive Patterns of Replication in a Panel of Cell Types", *J. Exp. Med.*, 170: 1149-1163 (1989).
Connor, R.I., et al., "Vpr is Required for Efficient Replication of Human Immunodeficiency Virus Type-1 in Mononuclear Phagocytes", *Virology*, 206: 935-944 (1995).

(Continued)

*Primary Examiner* — Jeffrey Parkin
(74) *Attorney, Agent, or Firm* — Hamilton, Brook, Smith & Reynolds, P.C.

(57) ABSTRACT

The invention is directed to a chimeric gammaretrovirus comprising an gammaretroviral virion which contains a lentiviral Vpx protein and methods of use thereof. In a particular aspect, the chimeric gammaretrovirus is a chimeric murine leukemia virus (MLV) comprising an MLV virion which contains a lentiviral Vpx protein. The invention is also directed to use of the chimeric gammaretrovirus to produce a MLV that can transduce a non-dividing cell (G1/S/G2), transduce a non-dividing cell; enhance the ability of a MLV to transduce a non-dividing cell; transduce a quiescent (G0) cell; and enhance the ability of a human immunodeficiency virus 1 (HIV-1) to transduce a quiescent (G0) cell.

22 Claims, 10 Drawing Sheets

(56) References Cited

PUBLICATIONS

Diamond, T.L., et al., "Macrophage Tropism of HIV-1 Depends on Efficient Cellular dNTP Utilization by Reverse Transcriptase", *Journal of Biological Chemistry*, 279(49): 51545-51553 (2004).

Eisert, V., et al., "Analysis of Cellular Factors Influencing the Replication of Human Immunodeficiency Virus Type 1 in Human Macrophages Derived from Blood of Different Healthy Donors", *Virology*, 286: 31-44 (2001).

Ellery, P.J., et al. "The CD16+ Monocyte Subset is More Permissive to Infection and Preferentially Harbors HIV-1 In Vivo", *The Journal of Immunology*, 178: 6581-6589 (2007).

Fletcher, T.M., et al., "Nuclear Import and Cell Cycle Arrest Functions of the HIV-1 Vpr Protein are Encoded by Two Separate Genes in HIV-2/SIV$_{sm}$", *The EMBO Journal*, 15(22): 6155-6165 (1996).

Gartner, S., et al., "The Role of Mononuclear Phagocytes in HTLV-III/LAV Infection", *Science*, 233: 215-219 (1986).

González-Scarano, F. And Martin-Garcia, J., "The Neuropathogenesis of Aids", *Nature Reviews Immunology*, 5: 69-81 (2005).

Goujon, C., et al., "Characterization of Simian Immunodeficiency Virus SIV$_{sm}$/Human Immunodeficiency Virus Type 2 Vpx Function in Human Myeloid Cells", *Journal of Virology*, 82(24): 12335-12345 (2008).

Heinzinger, N.K., et al., "The Vpr Protein of Human Immunodeficiency Virus Type 1 Influences Nuclear Localization of Viral Nucleic Acids in Nondividing Host Cells", *Proc. Natl. Acad. Sci.*, 91: 7311-7315 (1994).

Henderson, L.E., et al., "Isolation and Characterization of a Novel Protein (X-ORF Product) from SIV and HIV-2", *Science*, 241: 199-201 (1988).

Jarrosson-Wuilleme, L., et al., "Transduction of Nondividing Human Macrophages with Gamaretrovirus-Derived Vectors", *Journal of Virology*, 80(3): 1152-1159 (2006).

Kaushik, R., et al., "A Cellular Restriction Dictates the Permissivity of Nondividing Monocytes/Macrophages to Lentivirus and Gammaretrovirus Infection", *Cell*, 6: 68-80 (2009).

Lewis, P., et al. "Human Immunodeficiency Virus Infection of Cells Arrested in the Cell Cycle", *The EMBO Journal*, 11(8): 3053-3058 (1992).

Lewis, P.F. and Emerman, M., "Passage Through Mitosis is Required for Oncoretroviruses but Not for the Human Immunodeficiency Virus", *Journal of Virology*, 68(1): 510-516 (1994).

Malim, M.H. and Emerman, M., "HIV-1 Accessory Proteins-Ensuring Viral Survival in a Hostile Environment", *Cell*, 3: 388-398 (2008).

Münk, C., et al., "A Dominant Block to HIV-1 Replication at Reverse Transcription in Simian Cells", *PNAS*, 99(21): 13843-13848 (2002).

Naif, H.M., et al.,"CCR5 Expression Correlates with Susceptibility of Maturing Monocytes to Human Immunodeficiency Virus Type 1 Infection", *Journal of Virology*, 72(1): 830-836 (1998).

Neil, S., et al., "Postentry Restriction to Human Immunodeficiency Virus-Base Vector Transduction in Human Monocytes", *Journal of Virology*, 75(12): 5448-5456 (2001).

O'Brien, W.A., et al., "Kinetics of Human Immunodeficiency Virus Type 1 Reverse Transcription in Blood Mononuclear Phagocytes are Slowed by Limitations of Nucleotide Precursors", *Journal of Virology*, 68(2): 1258-1263 (1994).

Pancio, H. and Ratner, L., "Human Immunodeficiency Virus Type 2 Vpx-Gag Interaction", *Journal of Virology*, 72(6): 5271-5275 (1998).

Paxton, W., et al., "Incorporation of Vpr into Human Immunodeficiency Virus Type 1 Virions: Requirement for the p6 Region of gag and Mutational Analysis", *Journal of Virology*, 67(12): 7229-7237 (1993).

Peng, G, et al., "Induction of APOBEC3 Family Proteins, a Defensive Maneuver Underlying Interferon-Induces Anti-HIV-1 Activity", *The Journal of Experimental Medicine*, 203(1): 41-46 (2006).

Peng, G., et al., "Myeloid Differentiation and Susceptibility to HIV-1 are Linked to APOBEC3 Expression", *Blood*, 110(1): 393-400 (2007).

Rich, E.A., et al., "Increased Susceptibility of Differentiated Mononuclear Phagocytes to Productive Infection with Human Immunodeficiency Virus-1 (HIV-1)", *J. Clin. Inves.*, 89: 176-183 (1992).

Ringler, D.J., et al., "Cellular Localization of Simian Immunodeficiency Virus in Lymphoid Tissues", *American Journal of Pathology*, 134(2): 373-383 (1989).

Roe, T.Y., et al., "Integration of Murine Leukemia Virus DNA Depends on Mitosis", *The EMBO Journal*, 12(5): 2099-2108 (1993).

Sharova, N., et al., "Primate Lentiviral Vpx Commandeers DDB1 to Counteract a Macrophage Restriction", *PLOS Pathogens*, 4(5): e1000057, 12 pages, (2008).

Sharp, P.M., et al., "Gene Acquisition in HIV and SIV", *Nature*, 383: 586-587 (1996).

Sheehy, A.M., et al., "Isolation of a Human Gene that Inhibits HIV-1 Infection and is Suppressed by the Viral Vif Protein", *Nature*, 418: 646-650 (2002).

Sonza, S., et al., "Human Immunodeficiency Virus Type 1 Replication is Blocked Prior to Reverse Transcription and Integration in Freshly Isolated Peripheral Blood Monocytes", *Journal of Virology*, 70(6): 3863-3869 (1996).

Srivastava, S., "Lentiviral Vpx Accessory Factor Targets VprBP/DCAF1 Substrate Adaptor for Cullin 4 E3 Ubiquitin Ligase to Enable Macrophage Infection", *PLOS Pathogens*, 4(5): e1000059, 12 pages (2008).

Suzuki, Y. and Craigie, R., et al., "The Road to Chromatin—Nuclear Entry of Retroviruses", *Nature Reviews Microbiology*, 5: 187-196 (2007).

Triques. K., and Stevenson, M., "Characterization of Restrictions to Human Immunodeficiency Virus Type 1 Infection of Monocytes", *Journal of Virology*, 78(10): 5523-5527 (2004).

Tristem, M., et al.,"Evolution of the Primate Lentiviruses: Evidence from Vpx and Vpr", *The EMBO Journal*, 11(9): 3405-3412 (1992).

Weinberg, J.B., et al., "Productive Human Immunodeficiency Virus Type 1 (HIV-1) Infection of Nonproliferating Human Monocytes", *J. Exp. Med.*, 174: 1477-1482 (1991).

Wolfrum, N., et al., "Impact of Viral Accessory Proteins of SIVsm-mPBj on Early Steps of Infection of Quiescent Cells", *Virology*, 364: 330-341 (2007).

Wu, X., et al., "Localization of the Vpx Packaging Signal within the C Terminus of the Human Immunodeficiency Virus Type 2 Gag Precursor Protein", *Journal of Virology*, 68(10): 6161-6169 (1994).

Yamashita, M. and Emerman, M., "Retroviral Infection of Non-Dividing Cells: Old and New Prespectives", *Virology*, 344: 88-93 (2006).

Yamashita, M., et al.,"Evidence for Direct Involvement of the Caspid Protein in HIV Infection of Nondividing Cells", *PLOS Pathogens*, 3(10): 1502-1510, e156, (2007).

Zennou, V., et al., "HIV-1 Genome Nuclear Import is Mediated by a Central DNA Flap", *Cell*, 101: 173-185 (2000).

\* cited by examiner

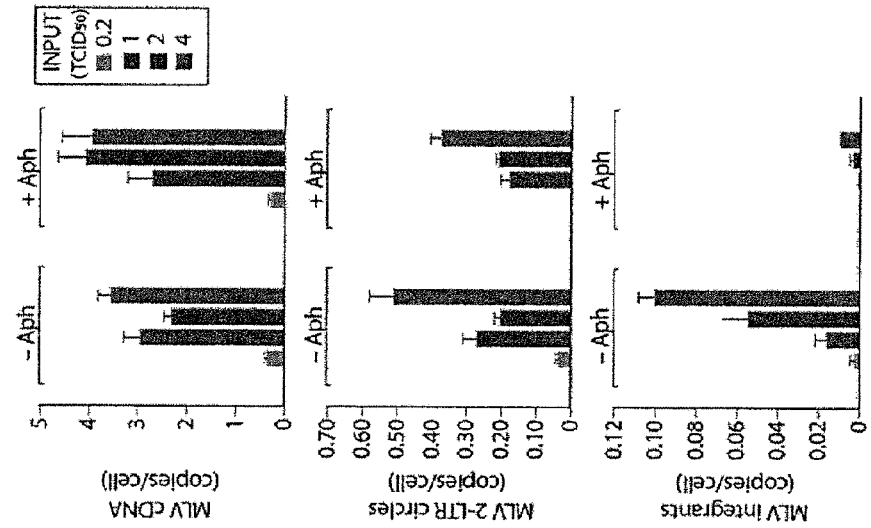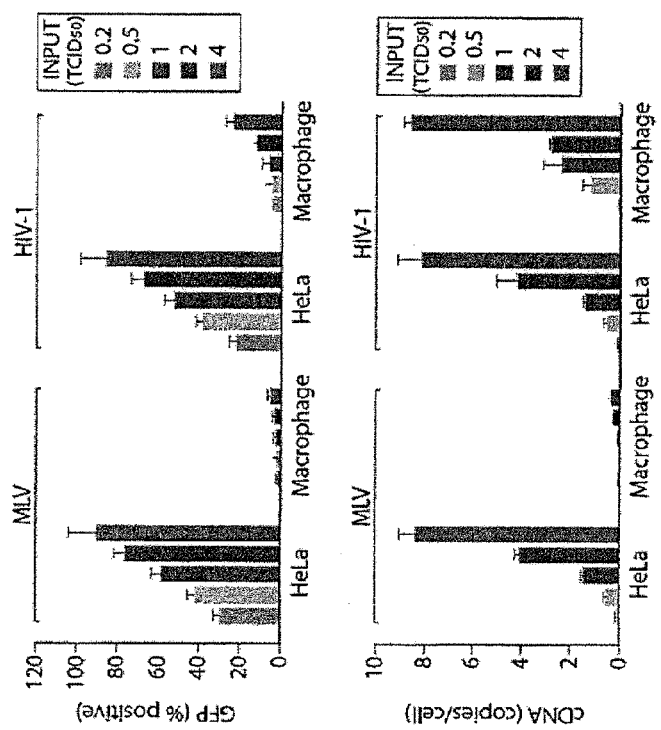

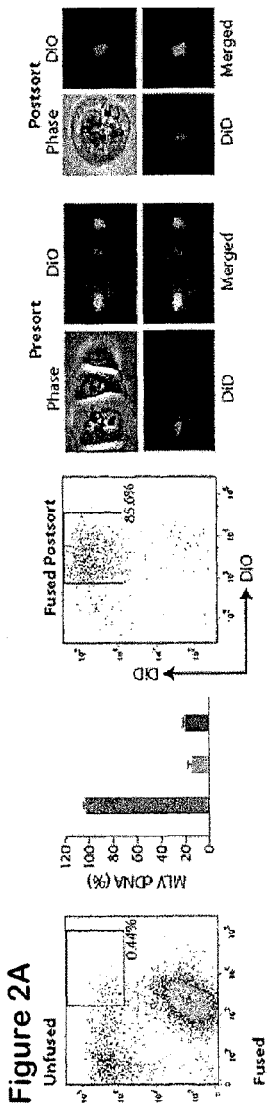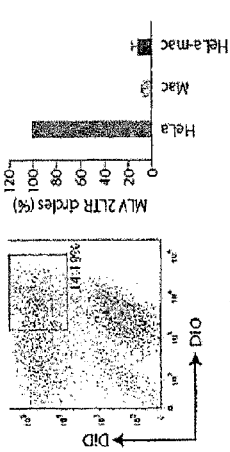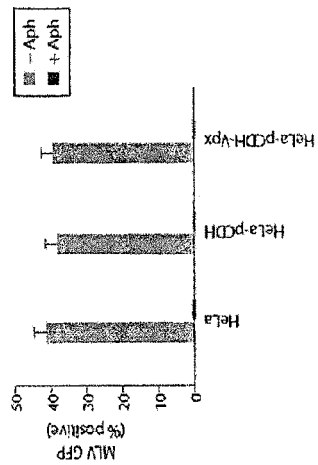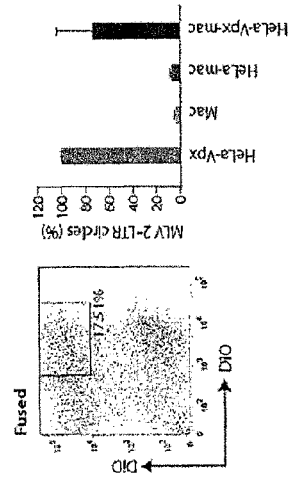

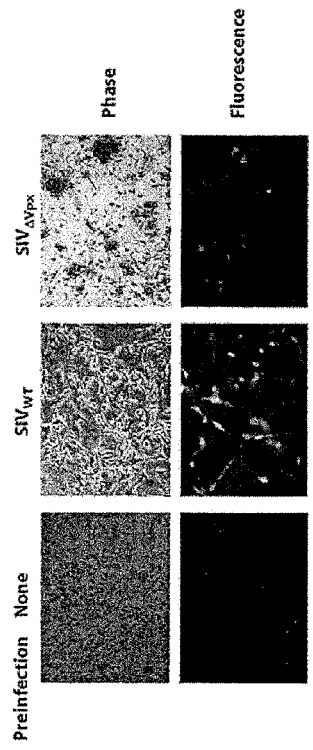
Figure 3A
Figure 3B
Figure 3C
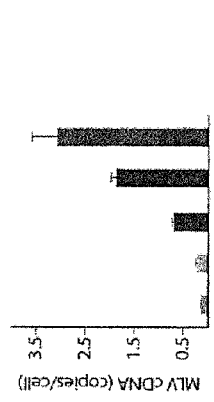
Figure 3D
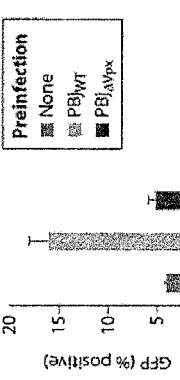
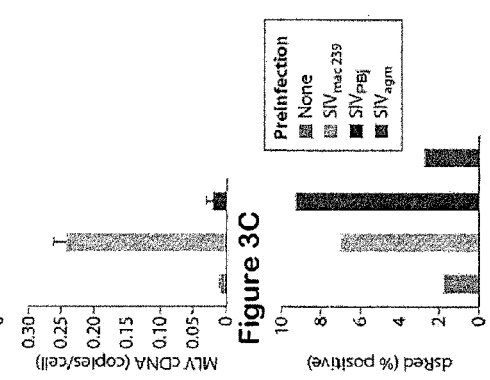
Figure 3E

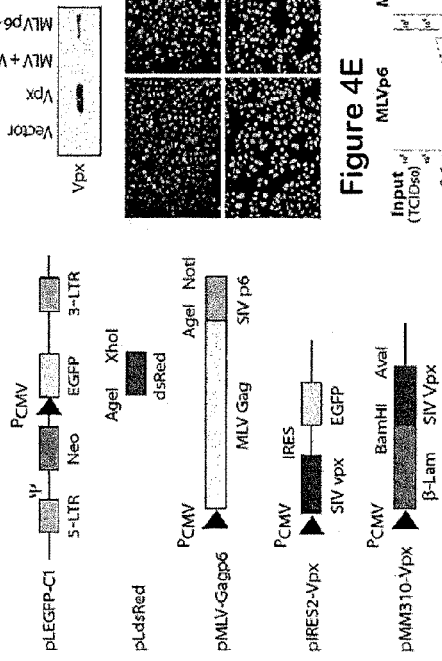
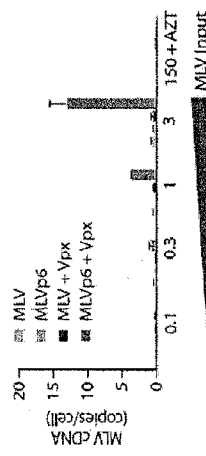
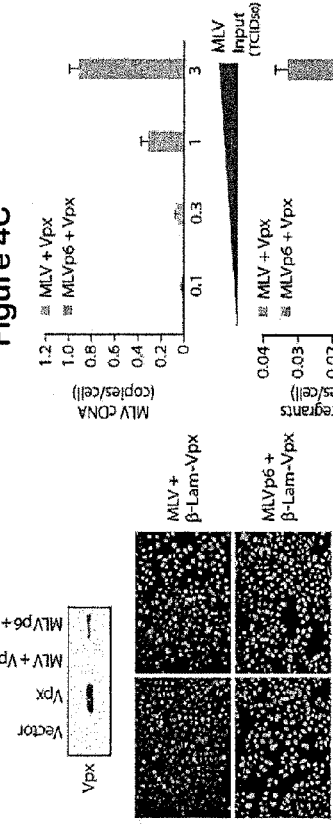
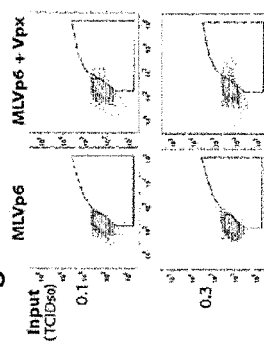
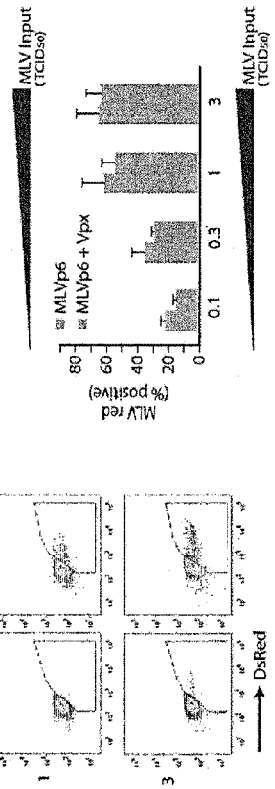
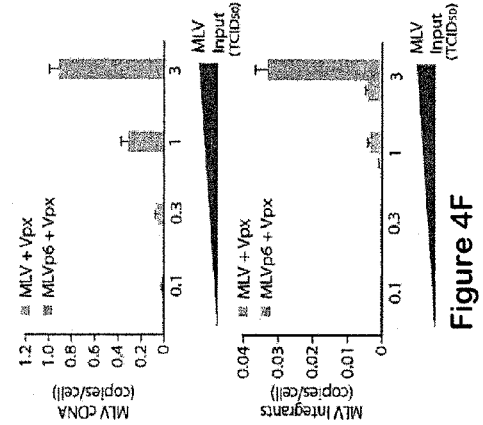
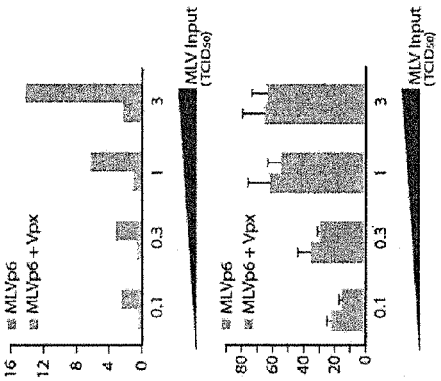

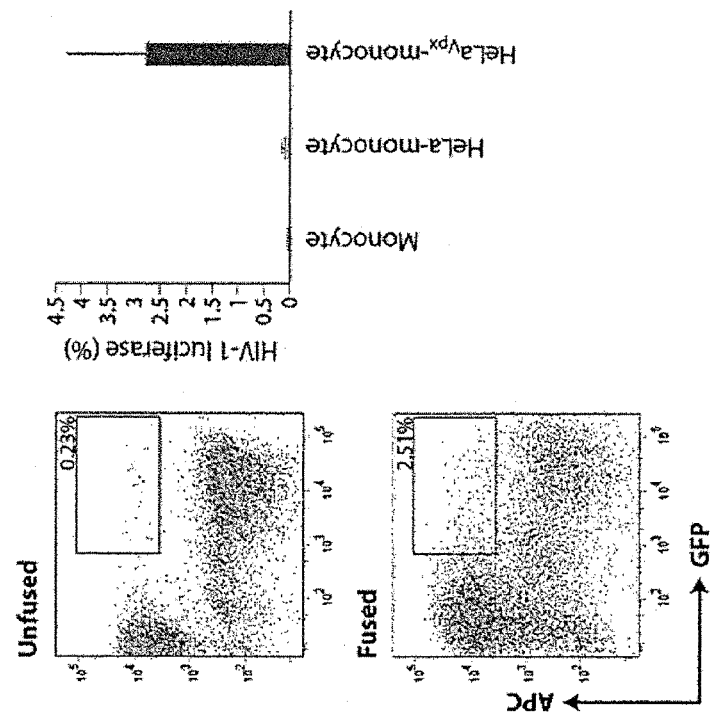
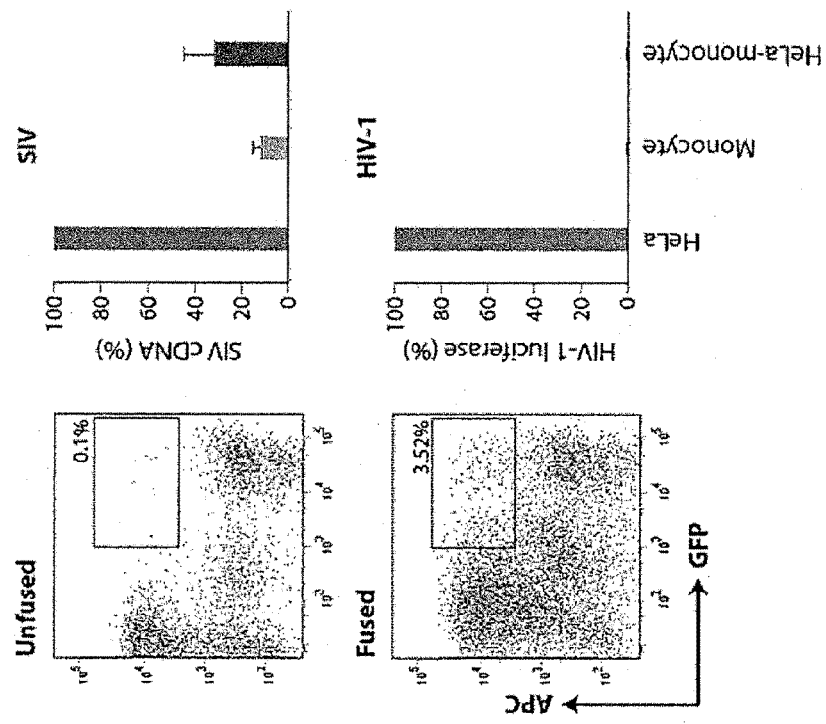

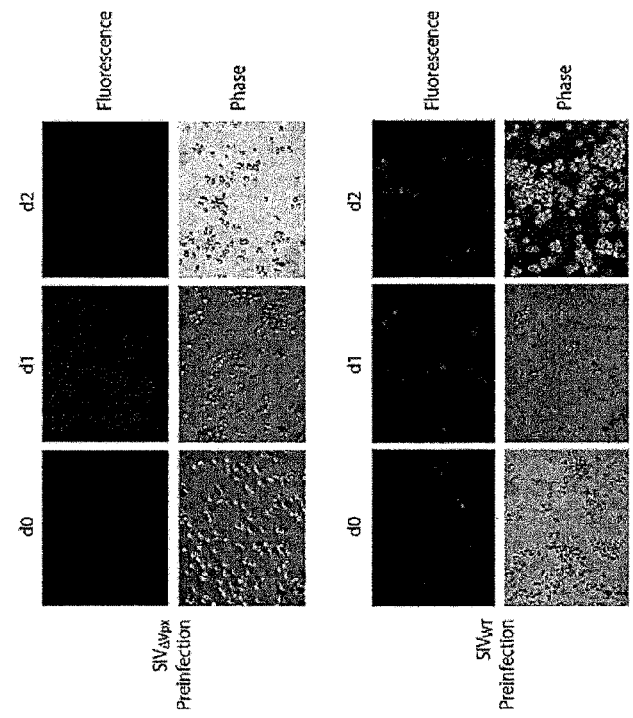
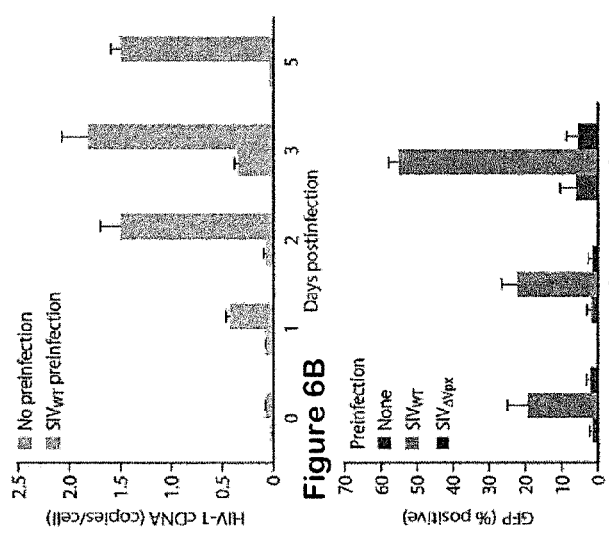
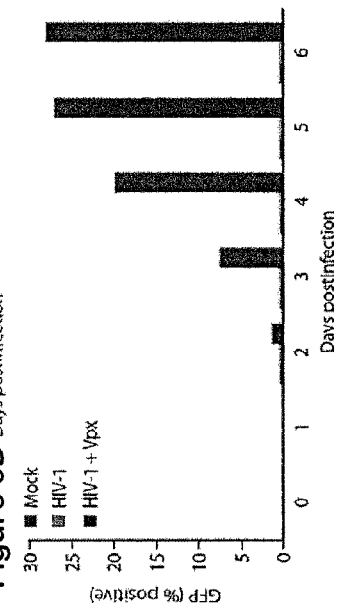
Figure 6A
Figure 6B
Figure 6C
Figure 6D
Figure 6E

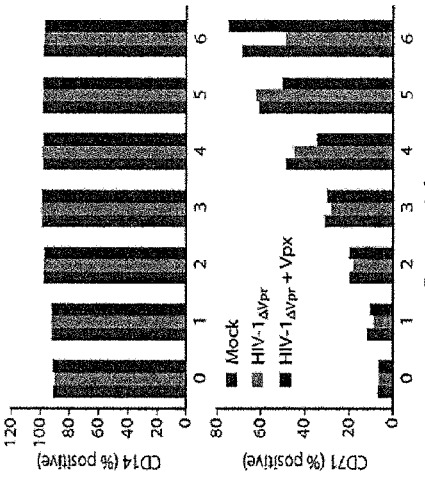
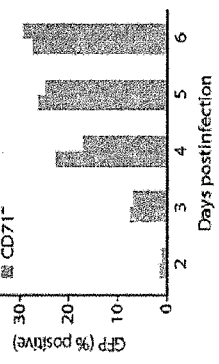
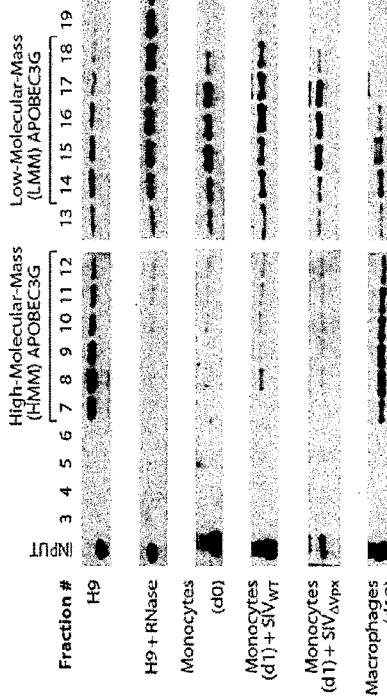
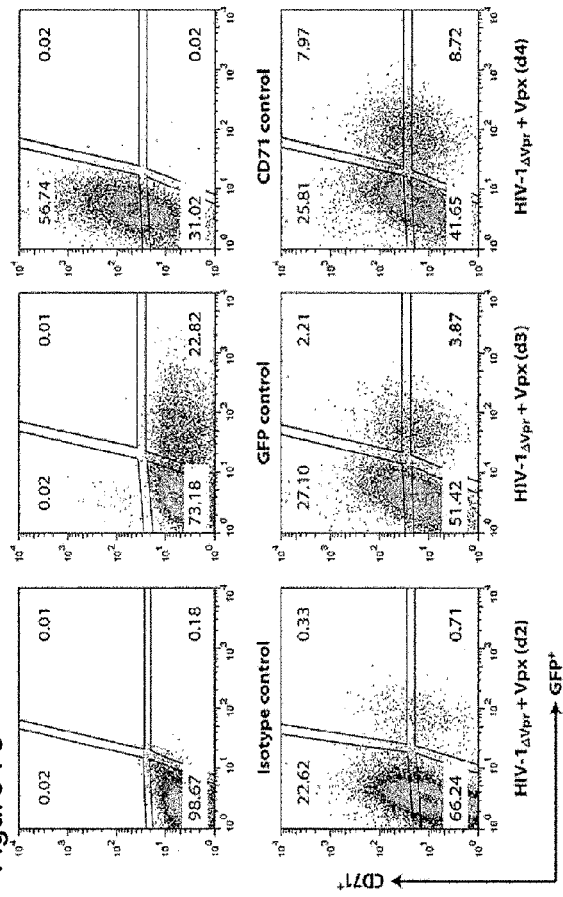
Figure 7A
Figure 7B
Figure 7C
Figure 7D

Figure 10

```
Pbj p6 region:
                         Vpx-packaging domain
451 PMAQMPQGLT PTAPPEDPAV DLLKNYMKMG RRQRENRERP YKEVTEDLLH
LNSLFGEDQ 519
```

HIV-1 p6 region:

```
                                          Vpr-binding domain
449 LQSRPEPTAP PEESFRSGVE TTTPPQKQEP IDKELYPLTS LRSLFGNDPS
SQ 500
```

The bold letters aa in HIV-1 p6 has been shown essential for Vpr packaging (Zhu, Zhao, retrovirology 2004; FxFG domain) and ELY has been shown to interact with vpr by NMR studies.

SEQUENCE LISTING

```
<160> NUMBER OF SEQ ID NOS: 5

<210> SEQ ID NO 1
<211> LENGTH: 112
<212> TYPE: PRT
<213> ORGANISM: unknown
<220> FEATURE:
<223> OTHER INFORMATION: amino acid sequence of Vpx protein
<220> FEATURE:
<221> NAME/KEY: VARIANT
<222> LOCATION: 3, 18, 29, 52, 69
<223> OTHER INFORMATION: Xaa = Any Amino Acid
<220> FEATURE:
<221> NAME/KEY: VARIANT
<222> LOCATION: 3, 18, 29, 52, 69
<223> OTHER INFORMATION: Xaa = Any Amino Acid
<220> FEATURE:
<221> NAME/KEY: VARIANT
<222> LOCATION: 3, 18, 29, 52, 69
<223> OTHER INFORMATION: Xaa = Any Amino Acid

<400> SEQUENCE: 1

Met Ser Xaa Pro Arg Glu Arg Ile Pro Pro Gly Asn Ser Gly Glu Glu
 1               5                  10                  15

Thr Xaa Gly Glu Ala Phe Asp Trp Leu His Arg Thr Xaa Glu Glu Ile
            20                  25                  30

Asn Arg Ala Ala Val Asn His Leu Pro Arg Glu Leu Ile Phe Gln Val
        35                  40                  45

Trp Arg Arg Xaa Trp Glu Tyr Trp His Asp Glu Met Gly Met Ser Val
    50                  55                  60

Ser Tyr Thr Lys Xaa Arg Tyr Leu Cys Leu Ile Gln Lys Ala Leu Phe
65                  70                  75                  80

Met His Cys Lys Lys Gly Cys Arg Cys Leu Gly Gly Glu His Gly Ala
                85                  90                  95

Gly Gly Trp Arg Pro Gly Pro Pro Pro Pro Pro Gly Leu Ala
            100                 105                 110
```

```
<210> SEQ ID NO 2
<211> LENGTH: 112
<212> TYPE: PRT
<213> ORGANISM: unknown
<220> FEATURE:
<223> OTHER INFORMATION: amino acid sequence of Vpx Protein

<400> SEQUENCE: 2

Met Ser Asp Pro Arg Glu Arg Ile Pro Pro Gly Asn Ser Gly Glu Glu
 1               5                  10                  15

Thr Ile Gly Glu Ala Phe Asp Trp Leu His Arg Thr Val Glu Glu Ile
            20                  25                  30

Asn Arg Ala Ala Val Asn His Leu Pro Arg Glu Leu Ile Phe Gln Val
        35                  40                  45

Trp Arg Arg Ser Trp Glu Tyr Trp His Asp Glu Met Gly Met Ser Val
 50                  55                  60

Ser Tyr Thr Lys Tyr Arg Tyr Leu Cys Leu Ile Gln Lys Ala Met Phe
65                  70                  75                  80

Met His Cys Lys Lys Gly Cys Arg Cys Leu Gly Gly Glu His Gly Ala
                85                  90                  95

Gly Gly Trp Arg Pro Gly Pro Pro Pro Pro Pro Gly Leu Ala
            100                 105                 110

<210> SEQ ID NO 3
<211> LENGTH: 790
<212> TYPE: PRT
<213> ORGANISM: unknown
<220> FEATURE:
<223> OTHER INFORMATION: amino acid sequence of the lentiviral gag
      Protein

<400> SEQUENCE: 3

Met Phe Ile Pro Leu Ile Phe Leu Pro Gln Leu Leu Gly Asn Val Leu
 1               5                  10                  15

Val Cys Val Leu Ala His His Phe Gly Lys Glu Phe Met Gly Gln Thr
            20                  25                  30

Val Thr Thr Pro Leu Ser Leu Thr Leu Gly His Trp Lys Asp Val Glu
        35                  40                  45

Arg Ile Ala His Asn Gln Ser Val Asp Val Lys Lys Arg Arg Trp Val
 50                  55                  60

Thr Phe Cys Ser Ala Glu Trp Pro Thr Phe Asn Val Gly Trp Pro Arg
65                  70                  75                  80

Asp Gly Thr Phe Asn Arg Asp Leu Ile Thr Gln Val Lys Ile Lys Val
                85                  90                  95

Phe Ser Pro Gly Pro His Gly His Pro Asp Gln Val Pro Tyr Ile Val
            100                 105                 110

Thr Trp Glu Ala Leu Ala Phe Asp Pro Pro Trp Val Lys Pro Phe
        115                 120                 125

Val His Pro Lys Pro Pro Pro Leu Pro Pro Ser Ala Pro Ser Leu
 130                 135                 140

Pro Leu Glu Pro Pro Arg Ser Thr Pro Arg Ser Ser Leu Tyr Pro
145                 150                 155                 160

Ala Leu Thr Pro Ser Leu Gly Ala Lys Pro Lys Pro Gln Val Leu Ser
                165                 170                 175

Asp Ser Gly Gly Pro Leu Ile Asp Leu Leu Thr Glu Asp Pro Pro
            180                 185                 190

Tyr Arg Asp Pro Arg Pro Pro Pro Ser Asp Arg Asp Gly Asn Gly Gly
```

-continued

```
            195                 200                 205
Glu Ala Thr Pro Ala Gly Glu Ala Pro Asp Pro Ser Pro Met Ala Ser
210                 215                 220
Arg Leu Arg Gly Arg Arg Glu Pro Pro Val Ala Asp Ser Thr Thr Ser
225                 230                 235                 240
Gln Ala Phe Pro Leu Arg Ala Gly Gly Asn Gly Gln Leu Gln Tyr Trp
                    245                 250                 255
Pro Phe Ser Ser Ser Asp Leu Tyr Asn Trp Lys Asn Asn Asn Pro Ser
                260                 265                 270
Phe Ser Glu Asp Pro Gly Lys Leu Thr Ala Leu Ile Glu Ser Val Leu
            275                 280                 285
Ile Thr His Gln Pro Thr Trp Asp Asp Cys Gln Gln Leu Leu Gly Thr
        290                 295                 300
Leu Leu Thr Gly Glu Glu Lys Gln Arg Val Leu Leu Glu Ala Arg Lys
305                 310                 315                 320
Ala Val Arg Gly Asp Asp Gly Arg Pro Thr Gln Leu Pro Asn Glu Val
                    325                 330                 335
Asp Ala Ala Phe Pro Leu Glu Arg Pro Asp Trp Asp Tyr Thr Thr Gln
                340                 345                 350
Ala Gly Arg Asn His Leu Val His Tyr Arg Gln Leu Leu Leu Ala Gly
            355                 360                 365
Leu Gln Asn Ala Gly Arg Ser Pro Thr Asn Leu Ala Lys Val Lys Gly
370                 375                 380
Ile Thr Gln Gly Pro Asn Glu Ser Pro Ser Ala Phe Leu Glu Arg Leu
385                 390                 395                 400
Lys Glu Ala Tyr Arg Arg Tyr Thr Pro Tyr Asp Pro Glu Asp Pro Gly
                    405                 410                 415
Gln Glu Thr Asn Val Ser Met Ser Phe Ile Trp Gln Ser Ala Pro Asp
                420                 425                 430
Ile Gly Arg Lys Leu Glu Arg Leu Glu Asp Leu Lys Asn Lys Thr Leu
            435                 440                 445
Gly Asp Leu Val Arg Glu Ala Glu Lys Ile Phe Asn Lys Arg Glu Thr
        450                 455                 460
Pro Glu Glu Arg Glu Glu Arg Ile Arg Arg Glu Thr Glu Glu Lys Glu
465                 470                 475                 480
Glu Arg Arg Arg Thr Glu Asp Glu Gln Lys Glu Lys Glu Arg Asp Arg
                    485                 490                 495
Arg Arg His Arg Glu Met Ser Lys Leu Leu Ala Thr Val Val Ser Gly
                500                 505                 510
Gln Lys Gln Asp Arg Gln Gly Gly Glu Arg Arg Arg Ser Gln Leu Asp
            515                 520                 525
Arg Asp Gln Cys Ala Tyr Cys Lys Glu Lys Gly His Trp Ala Lys Asp
        530                 535                 540
Cys Pro Lys Lys Pro Arg Gly Pro Arg Gly Pro Arg Pro Gln Pro Val
545                 550                 555                 560
Ala Thr Met Ala Ser Ser Glu Asp Val Ile Lys Glu Phe Met Arg Phe
                    565                 570                 575
Lys Val Arg Met Glu Gly Ser Val Asn Gly His Glu Phe Glu Ile Glu
                580                 585                 590
Gly Glu Gly Glu Gly Arg Pro Tyr Glu Gly Thr Gln Thr Ala Lys Leu
            595                 600                 605
Lys Val Thr Lys Gly Gly Pro Leu Pro Phe Ala Trp Asp Ile Leu Ser
        610                 615                 620
```

```
Pro Gln Phe Gln Tyr Gly Ser Lys Ala Tyr Val Lys His Pro Ala Asp
625                 630                 635                 640

Ile Pro Asp Tyr Leu Lys Leu Ser Phe Pro Glu Gly Phe Lys Trp Glu
            645                 650                 655

Arg Val Met Asn Phe Glu Asp Gly Gly Val Val Thr Val Thr Gln Asp
        660                 665                 670

Ser Ser Leu Gln Asp Gly Glu Phe Ile Tyr Lys Val Lys Leu Arg Gly
            675                 680                 685

Thr Asn Phe Pro Ser Asp Gly Pro Val Met Gln Lys Lys Thr Met Gly
    690                 695                 700

Trp Glu Ala Ser Thr Glu Arg Met Tyr Pro Glu Asp Gly Ala Leu Lys
705                 710                 715                 720

Gly Glu Ile Lys Met Arg Leu Lys Leu Lys Asp Gly Gly His Tyr Asp
                725                 730                 735

Ala Glu Val Lys Thr Thr Tyr Met Ala Lys Lys Pro Val Gln Leu Pro
            740                 745                 750

Gly Ala Tyr Lys Thr Asp Ile Lys Leu Asp Ile Thr Ser His Asn Glu
            755                 760                 765

Asp Tyr Thr Ile Val Glu Gln Tyr Glu Arg Ala Glu Gly Arg His Ser
    770                 775                 780

Thr Gly Ala Leu Tyr Lys
785                 790

<210> SEQ ID NO 4
<211> LENGTH: 59
<212> TYPE: PRT
<213> ORGANISM: unknown
<220> FEATURE:
<223> OTHER INFORMATION: amino acid sequence of Pbj p6 region

<400> SEQUENCE: 4

Pro Met Ala Gln Met Pro Gln Gly Leu Thr Pro Thr Ala Pro Pro Glu
1               5                   10                  15

Asp Pro Ala Val Asp Leu Leu Lys Asn Tyr Met Lys Met Gly Arg Arg
            20                  25                  30

Gln Arg Glu Asn Arg Glu Arg Pro Tyr Lys Glu Val Thr Glu Asp Leu
        35                  40                  45

Leu His Leu Asn Ser Leu Phe Gly Glu Asp Gln
    50                  55

<210> SEQ ID NO 5
<211> LENGTH: 52
<212> TYPE: PRT
<213> ORGANISM: unknown
<220> FEATURE:
<223> OTHER INFORMATION: amino acid sequence of HIV-1 p6 region

<400> SEQUENCE: 5

Leu Gln Ser Arg Pro Glu Pro Thr Ala Pro Pro Glu Glu Ser Phe Arg
1               5                   10                  15

Ser Gly Val Glu Thr Thr Thr Pro Pro Gln Lys Gln Glu Pro Ile Asp
            20                  25                  30

Lys Glu Leu Tyr Pro Leu Thr Ser Leu Arg Ser Leu Phe Gly Asn Asp
            35                  40                  45

Pro Ser Ser Gln
    50
```

METHOD OF TRANSDUCING NON-DIVIDING MYELOID CELLS UTILIZING CHIMERIC MURINE LEUKEMIA VIRUSES CONTAINING VPX

RELATED APPLICATION(S)

This application claims the benefit of U.S. Provisional Application No. 61/284,996, filed on Dec. 30, 2009. The entire teachings of the above application(s) are incorporated herein by reference.

GOVERNMENT SUPPORT

The invention was made with government support under grant nos. RR011589 and AI037475 awarded by the National Institutes of Health. The Government has certain rights in the invention.

INCORPORATION BY REFERENCE OF MATERIAL IN ASCII TEXT FILE

This application incorporates by reference the Sequence Listing contained in the following ASCII text file:
a) File name: 07462004001 SEQLIST.txt; created Jan. 31, 2014, 11 KB in size.

BACKGROUND OF THE INVENTION

Primate lentiviruses including HIV-1 have evolved the capacity to transduce terminally differentiated, non-dividing cells and as a consequence, these viruses establish persistent infections of tissue macrophage and microglia in the host. In contrast, non-dividing cells are refractory to infection by retroviruses such as MLV.

A number of studies have examined obstacles to infection of non-dividing cells by retroviruses. These studies have been conducted with artificially growth-arrested cell lines. Whether similar blocks exist in natural, non-dividing cells such as macrophage has not been examined.

A better understanding of the obstacles of retroviruses to infect non-dividing cells is needed.

SUMMARY OF THE INVENTION

Primate lentiviruses, including HIV-1, transduce terminally differentiated, nondividing myeloid cells; however, these cells are refractory to infection by gammaretroviruses such as murine leukemia virus (MLV). Presented herein is evidence that a cellular restriction is the obstacle to transduction of macrophages by MLV. Neutralization of the restriction by Vpx, a primate lentiviral protein previously shown to protect primate lentiviruses from a macrophage restriction, rendered macrophages permissive to MLV infection. Further demonstrated is that this restriction prevents transduction of quiescent monocytes by HIV-1. Monocyte-HeLa heterokaryons were resistant to HIV-1 infection, while heterokaryons formed between monocytes and HeLa cells expressing Vpx were permissive to HIV-1 infection. Encapsidation of Vpx within HIV-1 virions conferred the ability to infect quiescent monocytes. Collectively, the results herein indicate that the relative ability of lentiviruses and gammaretroviruses to transduce nondividing myeloid cells is dependent upon their ability to neutralize a cellular restriction.

Accordingly, in one aspect, the invention is directed to a chimeric gammaretrovirus comprising an gammaretroviral virion which contains a lentiviral Vpx protein. In a particular aspect, the invention is directed to a chimeric murine leukemia virus (MLV) comprising an MLV virion which contains a lentiviral Vpx protein.

In another aspect, the invention is directed to a method of producing a gammaretrovirus that can transduce a non-dividing cell (G1/S/G2), comprising introducing a lentiviral Vpx protein into the virion of the gammaretrovirus, thereby producing a gammaretrovirus that can transduce a non-dividing cell. In a particular aspect, the invention is directed to a method of producing a murine leukemia virus (MLV) that can transduce a non-dividing cell (G1/S/G2), comprising introducing a lentiviral Vpx protein into the virion of the MLV, thereby producing a MLV that can transduce a non-dividing cell.

In another aspect, the invention is directed to a method of transducing a non-dividing cell comprising contacting the cell with a chimeric gammaretrovirus comprising a gammaretroviral virion which contains a lentiviral Vpx protein and maintaining the cell under conditions in which nucleic acid of the chimeric gammaretrovirus is transferred to the cell, thereby transducing the non-dividing cell. In a particular aspect, the invention is directed to a method of transducing a non-dividing cell comprising contacting the cell with a chimeric murine leukemia virus (MLV) comprising an MLV virion which contains a lentiviral Vpx protein and maintaining the cell under conditions in which nucleic acid of the chimeric MLV is transferred to the cell, thereby transducing the non-dividing cell.

In another aspect, the invention is directed to a method of enhancing the ability of a gammaretrovirus to transduce a non-dividing cell comprising contacting the cell with a chimeric gammaretrovirus comprising a gammaretroviral virion which contains a lentiviral Vpx protein and maintaining the cell under conditions in which nucleic acid of the chimeric gammaretrovirus is transferred to the cell, thereby enhancing the ability of a gammaretrovirus to transduce the non-dividing cell. In a particular aspect, the invention is directed to a method of enhancing the ability of a murine leukemia virus (MLV) to transduce a non-dividing cell comprising contacting the cell with a chimeric MLV comprising an MLV virion which contains a lentiviral Vpx protein and maintaining the cell under conditions in which nucleic acid of the chimeric MLV is transferred to the cell, thereby enhancing the ability of a MLV to transduce the non-dividing cell.

In another aspect, the invention is directed to a method of transducing a quiescent (G0) cell comprising contacting the cell with a chimeric human immunodeficiency virus 1 (HIV-1) comprising a lentiviral Vpx protein and maintaining the cell under conditions in which nucleic acid of the chimeric HIV-1 is transferred to the cell, thereby transducing the quiescent cell.

In another aspect, the invention is directed to a method of enhancing the ability of a human immunodeficiency virus 1 (HIV-1) to transduce a quiescent (G0) cell comprising contacting the cell with a chimeric HIV-1 comprising a lentiviral Vpx protein and maintaining the cell under conditions in which nucleic acid of the chimeric HIV-1 is transferred to the cell, thereby transducing the quiescent cell.

BRIEF DESCRIPTION OF THE DRAWINGS

FIGS. 1A-1C show that MLV Infection of Macrophages Is Blocked at or Prior to Reverse Transcription of Viral cDNA. FIGS. 1A and 1B are graphs showing terminally differentiated macrophages and HeLa cells were infected with MLV and HIV-1 variants expressing GFP at different levels of input virions. The frequency of GFP$^+$ cells (A) and viral cDNA copies (B) was determined 48 hr postinfection. FIG. 1C shows graphs of MLV infection of aphidicolin-treated and untreated HeLa cells. Viral cDNA (upper two panels) and viral integrants (lower panel) were determined at different levels of input virus based on tissue culture infectious dose$_{50}$ (TCID$_{50}$), where one TCID$_{50}$ is the amount of virus inoculum that yielded 50% transduction on HeLa cells. Error bars are SD of replicate samples from three independent experiments done on HeLa cells or macrophages from different donors.

FIGS. 2A-2C show a Restriction Prevents Transduction of Macrophages by MLV. FIG. 2A shows that heterokaryons were formed between primary macrophages and HeLa cells expressing fusogenic HN and F proteins of Newcastle disease virus (NDV). HeLa cells were stained with DiO (green), and macrophages were stained with DID (red), Double-stained heterokaryons were sorted by FACS as indicated by the gate (FIG. 2A). FACS profile of heterokaryons postsorting (fused postsort) is shown (middle panel) as are representative double-staining heterokaryons presort and postsort (right panels). Because of the lipophilic nature of DiO and DiD, fluorescence concentrates in lipid-rich regions in the center of the cell rather than being evenly distributed throughout the cell. Susceptibility of HeLa-macrophage (HeLa-mac) heterokaryons to MLV infection was compared with infection levels in HeLa and in macrophages. Infection was gauged from the levels of late MLV cDNAs and 2-LTR circle cDNAs. Values were expressed relative to those obtained for HeLa cells (error bars are SD from three independent experiments). FIG. 2B shows the susceptibility of HeLa-macrophage heterokaryons to MLV infection examined after expression of Vpx in HeLa cells, Double-stained cells were sorted by FACS as indicated by the gate, MLV infection in HeLa-macrophage heterokaryons and heterokaryons formed between macrophages and Vpx-expressing HeLa cells (HeLa-Vpx-mac) were gauged as outlined in (FIG. 2A) (error bars are SD of three independent experiments). FIG. 2C shows MLV infection of aphidicolin-treated (+Aph) and untreated (−Aph) HeLa cells transfected with a Vpx expression vector (pCDH-Vpx) or an empty vector (pCDH). Error bars are SD of replicate samples from two independent experiments done on HeLa cells.

FIGS. 3A-3E show Vpx. Permits Transduction of Macrophages by MLV in trans. FIG. 2A shows Vpx delivered to macrophages by wild-type SIV (SIV$_{WT}$) infection removes the block to synthesis of MLV cDNA in macrophages. Macrophages were initially infected with increasing titers of SIV$_{WT}$ and subsequently infected with MLV (four TCID$_{50}$) after 4 hr. Synthesis of MLV cDNA was assessed 48 hr after MLV infection. FIGS. 3B-3D show Vpx but not Vpr is necessary for the ability of SIV to remove the block to macrophage transduction by MLV. Macrophages were infected by SIV$_{WT}$ or SIV$_{\Delta Vpx}$ and subsequently infected by MLV-GFP (four TCID$_{50}$) after 4 hr. The frequency of GFP and viral cDNA copies was determined 48 hr postinfection (3B). Error bars in (3A) and (3B) are SD of replicate samples from three independent experiments done on macrophages from different donors. FIG. 3C shows the results of macrophages were infected with the indicated SIV infectious clones and then with MLV$_{dsRed}$. The efficiency of MLV transduction was assessed 48 hr after MLV infection. FIG. 3D shows a representative field of macrophages transduced by MLV-GFP. FIG. 3E shows transduction of macrophages by MLV occurs primarily in SIV-infected macrophages, SIV$_{GFP}$-infected macrophages were transduced with MLV$_{dsRed}$, and frequencies of coinfected cells were evaluated by FACS. FACS profiles of uninfected macrophages, MLV-transduced macrophages without prior SIV infection (MLV alone), or SIV$_{WT}$ without subsequent MLV infection (SIV$_{WT}$ alone) served as controls.

FIGS. 4A-4F show MLV Virions Encapsidating Vpx Exhibit a Lentiviral Phenotype. FIG. 4A is a schematic of vectors used for expression of Vpx and chimeric MLV gag proteins containing the p6 domain of SIV gag, which harbors the Vpx/Vpr packaging determinant. FIG. 4B shows packaging of Vpx within MLV virions harboring an SIV gag p6 domain. Upper panel: packaging of Vpx within MLV virions containing or lacking an SIV gag p6 domain was examined by western blotting with a Vpx-specific antibody. Lower panels: β-lactamase-Vpx fusion proteins were packaged in MLV variants containing or lacking the SIV gag p6 domain, and (β-lactamase activity was examined following infection of HeLa cells loaded with the β-lactamase substrate CCF2. FIG. 4C shows packaging of Vpx within chimeric MLV virions containing SIV gag p6 (MLVp6) removes a block to reverse transcription in macrophages, Macrophages were infected with increasing concentrations of MLVp6 with or without encapsidated Vpx, and viral cDNA synthesis (late cDNA, upper panel) and integration (lower panel) was assessed. FIGS. 4D-4F shows a p6 encapsidation signal and Vpx are required for MLV transduction of macrophages. MLV cDNA synthesis (4D) was examined after infection of macrophages with MLV and MLVp6 variants with and without Vpx. Infections carried out in the presence of AZT verified de novo synthesis of MLV cDNA. Error bars in (4C) and (4D) are SD of replicate samples from three independent experiments done on macrophages from different donors (4E). Packaging of Vpx permits transduction of primary macrophages by MLV. Macrophages were infected with increasing titers of chimeric MLV variants with and without Vpx as in (4C). Transduction was gauged by expression of dsRed from the MLV transgene. Frequencies of MLV transduction (dsRed expression) on macrophages (upper panel) and HeLa (lower panel) are indicated in (4F). Error bars are SD of replicate samples from three independent experiments done on macrophages or HeLa cells.

FIGS. 5A-5B shows transduction of Primary Monocytes by HIV-1 Is Blocked by a Restriction. FIG. 5A shows heterokaryons were formed between primary monocytes and HeLa cells using HVJ Envelope Cell Fusion kit (see Experimental Procedures). FAGS analysis of HeLa-monocyte heterokaryons (left panels) is shown. HeLa cells expressed GFP, and macrophages were stained with an APC-conjugated antibody to CD14. Double-stained cells were sorted as indicated by the gate. SIV infection was gauged from the levels of late cDNA, and HIV-1 infection was gauged from luciferase activity (right panels). Values were expressed relative to those obtained for HeLa cells. Error bars are SD of four independent experiments. FIG. 5B shows Vpx renders HeLa-monocyte heterokaryons permissive to HIV-1 infection. Heterokaryons were formed between primary monocytes and HeLa cells expressing Vpx as described in (5A). Susceptibility of HeLa-monocyte heterokaryons to HIV-1 infection was examined after expression of Vpx in HeLa cells. FAGS analysis of HeLa-Vpx-monocyte heterokaryons is shown in the left panels, Double-stained cells were sorted as indicated by the gate. Infection of monocytes and infection of HeLa-monocyte heterokaryons with and without Vpx was gauged by luciferase activity. Error bars are SD from two independent experiments.

FIGS. 6A-6E show Vpx Counteracts a Monocyte Restriction to HIV-1 Infection In trans. FIG. 6A shows infection of monocytes by SIV$_{WT}$ removes a reverse transcription block to subsequent infection by HIV-1. SIV$_{WT}$-infected monocytes were subsequently infected (4 hr later) by HIV-1 on the indicated intervals, and levels of HIV-1 cDNA synthesis were gauged 48 hr after HIV-1 infection. FIG. 6B shows prior infection by SIV$_{WT}$ but not SIV$_{\Delta Vpx}$ renders primary monocytes permissive to subsequent transduction by HIV-1. Monocytes were infected as in (6A). Transduction of HIV-1 (based on GFP expression) was assessed 72 hr after HIV-1 infection. FIG. 6C shows representative fields of primary monocytes following transduction by HIV-1-GFP. FIG. 6D shows HIV-1 virions encapsidating Vpx efficiently transduce primary monocytes. Monocytes were infected with HIV-1-GFP variants in which Vpx was packaged. Levels of transduction (percent of GFP$^+$ monocytes) were determined at the indicated intervals after monocyte infection. FIG. 6E shows transduction of monocytes with an HIV-1 lentivirus vector in which Vpx was or was not packaged. Monocytes were infected at the indicated intervals, and GFP expression was examined 72 hr postinfection. Error bars in (6A), (6B), and (6E) are SD of replicate samples from three independent experiments done on monocytes from different donors.

FIGS. 7A-7D shows Vpx Renders Monocytes Permissive to HIV-1 Infection without Inducing Monocyte Differentiation or APOBEC3G Distribution. FIG. 7A shows distribution of APOBEC3G between LMM and HMM nucleoprotein complexes in undifferentiated (d0) monocytes, differentiated (d10) macrophages, and SIV-infected monocytes. Distribution of APOBEC3G between H9 cell-derived HMM and LMM complexes before and after RNase treatment is shown for comparison. FIG. 7B shows Vpx does not affect differentiation status of monocytes in culture. Fresh monocytes were infected with HIV$_{\Delta Vpr}$ GFP that had or had not packaged Vpx, and the infection levels in monocyte/macrophage (CD14$^+$ and differentiated monocyte (CD71$^+$) subsets was determined by FACS at the indicated intervals post-infection. FIGS. 7C and 7D show HIV-1 with encapsidated Vpx equally transduces undifferentiated (CD71$^-$) and differentiated (CD71$^+$) monocyte populations. Monocytes were infected with HIV-1 in which Vpx had been packaged (lower three panels), and the frequencies of infected (GFP$^+$) CD71$^+$ macrophages and CD71$^-$ monocytes were determined by FACS. Upper three panels depict uninfected controls. FIG. 7D shows the frequency of HIV-1 infection in CD71$^+$ and CD71$^-$ cells at different intervals postinfection.

FIG. 8A shows pseudotyped SIV$_{\Delta Vpx}$ was produced in 293T cells by cotransfecting ΔVpx PBj 1.9 proviral DNA with pMD-G and increasing amount of a Vpx expression vector. The amount of packaged Vpx in the purified virions was determined by western blotting with a Vpx antibody and normalization with p27 by densitometry. The integrated density was measured by Scion Image software. FIG. 8B shows the infectivity of these viruses in primary macrophages was determined from quantitation of SIV 2-LTR cDNA 24 and 48 hr postinfection. PBj$_{WT}$ was used as positive control for this experiment. Error bars are SD of replicate samples from two independent experiments done on macrophages from different donors.

FIG. 10 shows the amino acid sequence of Pbj p6 region (SEQ ID NO: 4) wherein the Vpx-packaging domain is highlighted, and the amino acid sequence of the HIV-1 p6 region (SEQ ID NO: 5) wherein the Vpr-binding domain is highlighted; the bold letters in the HIV-1 p6 domain have been shown essential for Vpr packaging (Zhu, Zhao, Retrovirology (2004) and ELY has been shown to interact with Vpr by NMR studies.

DETAILED DESCRIPTION OF THE INVENTION

Figure 8A:
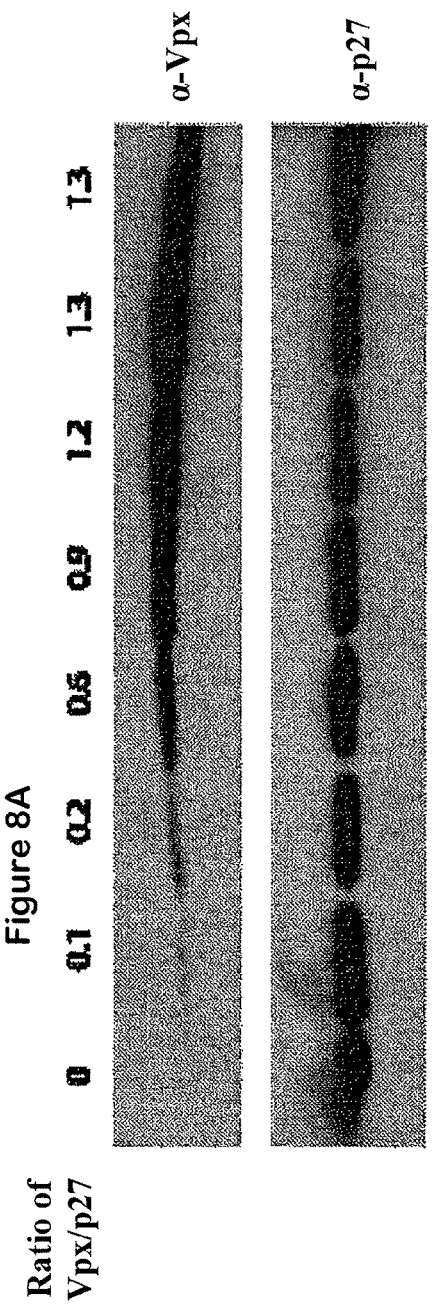
FIGS. 8A-8B show dose-dependent Ability of Packaged Vpx to Counteract a Macrophage Restriction.

A fundamental characteristic that distinguishes lentiviruses from simple gammaretroviruses is their capacity to infect nondividing cells (reviewed in Suzuki and Craigie, 2007; Yamashita and Emerman, 2006). Primate lentiviruses such as HIV-1 are able to transduce nondividing cells (Bukrinsky et al., 1992; Lewis et al., 1992), and this underscores their ability to transduce terminally differentiated nondividing cells, including macrophages, microglia, and dendritic cells, both in vitro and in vivo (Gartner et al., 1986; Ringler et al., 1989; Weinberg et al., 1991). In contrast, gammaretroviruses transduce cells in mitosis, and nondividing cells (in $G_1/S/G_2$ phase) are refractory to gammaretrovirus transduction (Bieniasz et al., 1995; Lewis et al., 1992; Lewis and Emerman, 1994; Roe et al., 1993). Furthermore, although lentiviruses have evolved the ability to infect terminally differentiated nonproliferating cells, quiescent cells ($G_o$) are refractory to lentivirus transduction. This is best exemplified by observations made with myeloid-lineage cells. Studies conducted with HIV-1 demonstrate that peripheral blood monocytes, which are the undifferentiated precursors to tissue macrophages, are highly refractory to infection (Collman et al., 1989; Di Marzio et al., 1998; Eisert et al., 2001; Naif et al., 1998; Neil et al., 2001; Rich et al., 1992; Sonza et al., 1996). Permissivity to HIV-1 infection is coordinated to the state of monocyte differentiation (Sonza et al., 1996; Triques and Stevenson, 2004).

The mechanisms underscoring the differential ability of gammaretroviruses and lentiviruses to transduce nondividing myeloid cells as well as the block to transduction of quiescent monocytes by lentiviruses are not well understood. Cell transduction by gammaretroviruses and lentiviruses requires synthesis of viral cDNA and translocation of viral cDNA to the nucleus in order for viral cDNA to integrate into cellular DNA. Synthesis of viral cDNA and transport of viral cDNA to the cell nucleus occurs within the context of a large (160 s) ribonucleoprotein reverse transcription/preintegration complex, which contains viral reverse transcriptase as well as the viral integrase that catalyzes formation of the integrated provirus (Bowerman et al., 1989). Therefore, transduction of a nondividing cell requires translocation of this complex across the nuclear envelope in order for viral cDNA to contact chromatin. One possible explanation for the differential ability of lentiviruses and gammaretroviruses to transduce nondividing cells is that reverse transcription complexes of lentiviruses harbor nucleophilic determinants that direct their nuclear translocation, whereas reverse transcription complexes of gammaretroviruses lack these determinants (reviewed in Suzuki and Craigie, 2007; Yamashita and Emerman, 2006).

A number of viral factors (reviewed in Suzuki and Craigie, *Nat Rev Microbiol*, 5, 187-196 (2007); Yamashita and Emerman, *Virology*, 344, 88-93 (2006)) have been implicated in promoting nuclear translocation of the lentiviral reverse transcription complex including a triple stranded viral DNA intermediate referred to as the central DNA flap (Zennou et al., *Cell*, 101, 173-185 (2000)). Viral proteins including integrase (Bouyac-Bertoia et al., *Mol Cell*, 7, 1025-1035 (2001)), the VprNpx accessory proteins (Fletcher et al., *EMBO Journal*, 15, 6155-6165 (1996); Heinzinger et al., *Proc Nat Acad Sci*

USA, 91, 7311-7315 (1994)), the matrix domain of Gag (Bukrinsky et al., Nature, 365, 666-669 (1993)) and the capsid domain within Gag (Yamashita et al., PLoS Pathog, 3, 1502-1510 (2007)) have been suggested to play a role in non-dividing cell infection by HIV-1. There is also biochemical evidence that lentiviral reverse transcriptases, unlike oncoretroviral reverse transcriptases, synthesize cDNA in the presence of low dNTP concentrations that are equivalent to those found in macrophage and this has been suggested to account for the differential ability of lentiviruses and retroviruses to transduce non-dividing macrophage (Diamond et al., J Biol Chem, 279, 51545-51553 (2004)). However, there is no consensus as to which, if any, of these viral factors are ultimately responsible for the inability of retroviruses and the ability of lentiviruses to transduce non-dividing cells.

A different set of factors has been proposed to regulate infection of quiescent monocytes by lentiviruses. $G_0$ monocytes have low intracellular dNTP levels (O'Brien et al., 1994; Triques and Stevenson, 2004), and this has been proposed to limit the efficiency of viral cDNA synthesis in these quiescent cells. The cytidine deaminase APOBEC3G, which is a target of the viral accessory protein Vif, has been shown to influence the permissivity of quiescent lymphocytes and monocytes to HIV-1 infection (Chiu et al., 2005; Ellery et al., 2007; Peng et al., 2006, 2007). APOBEC3G is sequestered in an enzymatically active low-molecular-mass (LMM) ribonucleoprotein complex or in an enzymatically inactive high-molecular-mass (HMM) complex. The LMM complex, which is the exclusive form in quiescent cells, has been shown to restrict infection of quiescent monocytes by HIV-1 (Chiu et al., 2005; Ellery et al., 2007; Peng et al., 2006).

A number of studies have suggested that the accessory proteins Vpr and Vpx of primate lentiviruses have evolved to specifically promote infection of nondividing myeloid-lineage cells (Balliet et al., 1994; Connor et al., 1995; Fletcher et al., 1996; Goujon et al., 2008; Heinzinger et al., 1994; Sharova et al., 2008; Srivastava et al., 2008). By generating heterokaryons between cells in which Vpx was dispensable for infection and primary macrophages in which Vpx is required for SIV infection, demonstrated herein is that macrophages harbor a dominant restriction and that this restriction is specifically counteracted by Vpx (Sharova et al., 2008). In the study provided herein, it is demonstrated that this restriction is an obstacle to transduction of terminally differentiated nondividing cells by gammaretroviruses. Furthermore, evidence that the ability of lentiviruses to transduce quiescent monocytes is regulated by this same restriction and that neutralization of the restriction in monocytes confers susceptibility to lentivirus infection is presented. Collectively, the results herein indicate that the relative ability of lentiviruses and gammaretroviruses to transduce nondividing myeloid cells is governed primarily by their ability to neutralize a restriction that is present within these cells.

Specifically, shown herein is that cellular restriction can be neutralized by Vpx, a primate lentiviral protein previously shown to protect primate lentiviruses from a macrophage restriction (Kaushik, R., et al., Cell Host & Microbe, 6:68-80 (July 2009); Kaushik, R., et al., Abstract 25, A Cellular Restriction Dictates the Cell-Cycle Dependence of Retrovirus Infection, 16$^{th}$ Conference on Retroviruses and Opportunistic Infections (Feb. 8-11, 2009); Stevenson, S., Top HIV Med, 17(2):30-34 (2009), all of which are incorporated by reference in their entirety herein). Vpx rendered macrophage permissive to MLV infection. Packaging of Vpx within MLV virions was sufficient to confer a lentivirus phenotype for MLV. As further shown herein, this restriction prevents transduction of quiescent monocytes by HIV-1. Monocyte-HeLa heterokaryons were resistant to HIV-1 infection while heterokaryons formed between monocytes and HeLa cells expressing Vpx were permissive to HIV-1 infection. Encapsidation of Vpx within HIV-1 virions conferred the ability to infect quiescent monocytes.

The results provided herein indicate that the relative ability of lentiviruses and retroviruses to transduce non-dividing, myeloid-cells is dependent upon their ability to neutralize a cellular restriction.

Recombinant vectors derived from gammaretroviruses such as murine leukemia virus (MLV) have been widely used to introduce genes in human gene therapy clinical trials and have shown the potential for therapeutic applications. The results herein show that packaging of Vpx within gammaretroviral virions (e.g., MLV virions) is sufficient to confer a lentivirus phenotype to the gammaretrovirus.

Accordingly, in one aspect, the invention is directed to chimeric gammaretroviruses having a virion which comprises all or a portion of a lentiviral Vpx protein.

As is apparent to those of skill in the art, a gammaretrovirus is a genus of viruses in the Retroviridae family. Examples of gammaretroviruses include the murine leukemia virus (MLV), the Abelson murine leukemia virus, the feline leukemia virus, the feline sarcoma virus, and the avian reticuloendotheliosis viruses. In a particular aspect, the invention is directed to a chimeric MLV comprising an MLV virion which contains all or a portion of a lentiviral Vpx protein.

As discussed supra, a Vpx protein is a lentiviral protein previously shown to protect lentiviruses from a macrophage restriction. Lentiviruses are also a genus of viruses in the Retroviridae family, characterized by a long incubation period. Human immunodeficiency virus (HIV such as HIV-1, HIV-2), simian immunodeficiency virus (SIV such as $SIV_{smm}$, $SIV_{mac}$), feline immunodeficiency virus (FIV), puma lentivirus, bovine immunodeficiency virus, equine infectious anemia virus, caprine arthritis encephalitis and visna/maedi virus are all examples of lentiviruses. Examples of lentiviruses which express the Vpx protein include HIV-2 and primate lentiviruses (e.g., SIV).

As will be understood by those of skill in the art, any suitable Vpx protein can be used in the compositions and methods described herein. In one aspect, the Vpx protein is a lentiviral Vpx protein. In a particular embodiment, the Vpx protein is a primate lentiviral SIV Vpx protein (e.g., $SIV_{smm}$ Vpx; $SIV_{mac}$ Vpx). In another aspect, the Vpx protein is an HIV-2 Vpx protein. In another aspect, the Vpx protein has an amino acid sequence comprising: MSXPRERIPP GNSGEETXGE AFDWLHRTXE EINRAAVNHL PRELIFQVWR RXWEYWHDEM GMSVSYTKXR YLCLIQKALF MHCKKGCRCL GGEHGAGGWR PGPPPPPPG LA (SEQ ID NO: 1); MSDPRERIPP GNSGEETIGE AFDWLHRTVE EINRAAVNHL PRELIFQVWR RSWEYWHDEM GMSVSYTKYR YLCLIQKAMF MHCKKGCRCL GGEHGAGGWR PGPPPPPPPG LA (SEQ ID NO: 2).

All or a portion (functional portion; biologically active portion) of a Vpx protein is incorporated into the virion of a gammeretrovirus to generate the chimeric gammetroviruses described herein. Portions of Vpx proteins are portions of Vpx that retain the biological activity of a Vpx protein (full length Vpx protein, wild type Vpx protein). As used herein the biological activity of a Vpx protein includes the activity which protects lentiviruses from a macrophage restriction.

As will be apparent to those of skill in the art, Vpx variants (alleles) and/or Vpx mutants that retain the biological activity of the Vpx protein can also be used in the compositions and methods provided herein.

Methods for assessing the biological activity of a portion of a Vpx protein and or a VPx variant or Vpx mutant for its ability to protect lentiviruses from a macrophage restriction are provided herein and other such methods are apparent to those of skill in the art. For example, a portion of a Vpx protein, a Vpx variant and/or a Vpx mutant can be incorporated into a MLV virion to generate a chimeric MLV as described herein. The resulting chimeric MLV can then be assessed for its ability to transduce a nondividing cell such as a monocyte or macrophage using assays described herein and in the art (e.g., Sharova, N., et al., *PLoS Pathogens,* 4(5):1-12 (2008) which is incorporated in its entirely herein by reference).

In a particular aspect, the chimeric gammaretrovirus further comprises components (e.g., determinants, accessory genes, accessory proteins) that enable, or assist in, the encapsidation of all or a portion of the Vpx protein into the chimeric gammaretroviral virion. An example of such a component is the p6 domain of a lentiviral gag protein which contains determinants for encapsidation of the Vpx protein. As will be apparent to those of skill in the art, variants (alleles) and/or mutants of these components that retain the biological activity of providing for encapsidation of all or a portion of the Vpx protein into the chimeric virion, can also be used in the compositions and methods provided herein. For example, the chimeric gammaretrovirus can further comprise all or a portion (functional portion; portion having biological activity), a variant and/or mutant of a lentiviral gag protein. In a particular aspect, the chimeric gammaretrovirus further comprises all or a portion of the p6 domain of a lentiviral gag protein. In another aspect, the lentiviral gag protein has an amino acid sequence comprising:

(SEQ ID NO: 3)
MFIPLIFLPQLLGNVLVCVLAHHFGKEFMGQTVTTPLSLTLGHWKDVE

RIAHNQSVDVKKRRWVTFCSAEWPTFNVGWPRDGTFNRDLITQVKIKV

FSPGPHGHPDQVPYIVTWEALAFDPPPWVKPFVHPKPPPPLPPSAPSL

PLEPPRSTPPRSSLYPALTPSLGAKPKPQVLSDSGGPLIDLLTEDPPP

YRDPRPPPSDRDGNGGEATPAGEAPDPSPMASRLRGRREPPVADSTTS

QAFPLRAGGNGQLQYWPFSSSDLYNWKNNNPSFSEDPGKLTALIESVL

ITHQPTWDDCQQLLGTLLTGEEKQRVLLEARKAVRGDDGRPTQLPNEV

DAAFPLERPDWDYTTQAGRNHLVHYRQLLLAGLQNAGRSPTNLAKVKG

ITQGPNESPSAFLERLKEAYRRYTPYDPEDPGQETNVSMSFIWQSAPD

IGRKLERLEDLKNKTLGDLVREAEKIFNKRETPEEREERIRRETEEKE

ERRRTEDEQKEKERDRRRHREMSKLLATVVSGQKQDRQGGERRRSQLD

RDQCAYCKEKGHWAKDCPKKPRGPRGPRPQPVATMASSEDVIKEFMRF

KVRMEGSVNGHEFEIEGEGEGRPYEGTQTAKLKVTKGGPLPFAWDILS

PQFQYGSKAYVKHPADIPDYLKLSFPEGFKWERVMNFEDGGVVTVTQD

SSLQDGEFIYKVKLRGTNFPSDGPVMQKKTMGWEASTERMYPEDGALK

GEIKMRLKLKDGGHYDAEVKTTYMAKKPVQLPGAYKTDIKLDITSHNE

DYTIVEQYERAEGRHSTGALYK.

Methods for assessing the biological activity of a portion of such a component and a variant or mutant for its ability to encapsidate the Vpx protein into a gammaretroviral virion are provided herein and other such methods are apparent to those of skill in the art.

As described herein, all or a portion of a Vpx protein is incorporated (packaged) into a gammaretroviral virion. In one aspect, all or a portion of the Vpx protein and/or all or a portion of an additional component that assists in the encapsidation of the Vpx protein into the gammaretroviral virion is fused to the C terminus of the gag protein of the gammaretrovirus. However, as understood by one of skill in the art, all or a portion of the Vpx protein and/or all or a portion of an additional component that assists in the encapsidation of the Vpx protein into the gammaretroviral virion can be fused to other regions or domains within the gammaretroviral virion.

As is also apparent to one of skill in the art, all or portion of the Vpx protein and/or additional components and mutants and variants thereof for use in the compositions and methods described herein can be isolated (purified; substantially purified) from their source of origin (e.g., retrovirus), chemically synthesized and/or recombinantly produced.

In another aspect, the invention is directed to a method of producing a gammaretrovirus that can transduce a non-dividing cell (G1/S/G2), comprising introducing a lentiviral Vpx protein into the virion of the gammaretrovirus, thereby producing a gammaretrovirus (a chimeric gammaretrovirus) that can transduce a non-dividing cell. In a particular aspect, the invention is directed to a method of producing a murine leukemia virus (MLV) that can transduce a non-dividing cell (G1/S/G2), comprising introducing a lentiviral Vpx protein into the virion of the MLV, thereby producing a MLV (a chimeric MLV) that can transduce a non-dividing cell.

As used herein, a non-dividing cell (G1/S/G2) can be a terminally differentiated cell. Examples of a terminally differentiated cell include a macrophage, a microglia, a dendritic cell, and a neuron.

As known to those of skill in the art, to transduce (transduction, infection) a cell refers to the ability to transfer viral genetic material to a cell (virus mediated transfer of genetic material).

In a particular aspect, the lentiviral Vpx protein is introduced into the virion of the gammaretrovirus (e.g., MLV) comprising (a) transfecting a gammaretroviral packaging cell line with one or more plasmids which express a fusion protein comprising the p6 domain of SIV fused to the C terminus of the gammaretroviral gag protein, and a Vpx expression vector; and (b) maintaining the packaging cell line under conditions in which the Vpx protein is packaged into gammaretrovirus virus particles wherein the lentiviral Vpx protein is fused to the C terminus of the gammaretroviral gag protein.

In another aspect, the invention is directed to a gammaretrovirus (e.g., chimeric MLV) that can transduce a non-dividing cell (G1/S/G2) produced by the methods described herein.

The chimeric gammaretroviruses described herein can be used in a variety of ways. Accordingly, in another aspect, the invention is directed to a method of transducing a non-dividing cell comprising contacting the cell with a chimeric gammaretrovirus (chimeric MLV) comprising a virion which contains a lentiviral Vpx protein and maintaining the cell under conditions in which nucleic acid of the chimeric gammaretrovirus is transferred to the cell, thereby transducing the non-dividing cell.

In yet another aspect, the invention is directed to a method of enhancing the ability of a gammaretrovirus (e.g., MLV) to transduce a non-dividing cell comprising contacting the cell with a chimeric gammaretrovirus which comprises a gammaretroviral virion which contains a lentiviral Vpx protein and maintaining the cell under conditions in which nucleic acid of the chimeric gammaretrovirus is transferred to the cell, thereby enhancing the ability of a gammaretrovirus to transduce the non-dividing cell.

As will be appreciated by those of skill in the art, the chimeric gammaretroviruses of the invention can further comprises an exogenous nucleic acid sequence (e.g., genmoic sequence, DNA, RNA, siRNA, shRNA, antisense RNA) to be expressed upon transduction of the chimeric gammaretrovirus into the non-dividing cell. As used herein, an exogenous sequence (e.g., non native sequence) refers to a nucleic acid sequence (e.g., an exogenous gene sequence) that encodes a protein that is not normally expressed, or is not expressed in significant amounts or to a measurable extent, in the cell. Thus, the chimeric gammaretroviruses can be used to introduce exogenous sequence into cells (e.g., a non-dividing cell). Examples of an exogenous sequence includes sequences which encode a therapeutic protein, a toxin, a fluorescent protein, and the like.

As discussed supra, Vpx rendered macrophage permissive to MLV infection. Packaging of Vpx within MLV virions was sufficient to confer a lentivirus phenotype for MLV. Also shown herein, was that this restriction prevents transduction of quiescent monocytes by HIV-1. Monocyte-HeLa heterokaryons were resistant to HIV-1 infection while heterokaryons formed between monocytes and HeLa cells expressing Vpx were permissive to HIV-1 infection. That is, encapsidation of Vpx within HIV-1 virions conferred the ability to infect quiescent monocytes.

Thus, in another aspect, the invention is directed to a method of producing a human immunodeficiency virus 1 (HIV-1) that can transduce a quiescent ($G_0$) cell, comprising introducing a lentiviral Vpx protein into the virion of the HIV, thereby producing a HIV that can transduce a quiescent cell.

In another aspect, the invention is directed to a method of transducing a quiescent (G0) cell comprising contacting the cell with a chimeric human immunodeficiency virus 1 (HIV-1) comprising a lentiviral Vpx protein and maintaining the cell under conditions in which nucleic acid of the chimeric HIV-1 is transferred to the cell, thereby transducing the quiescent cell.

In yet another aspect, the invention is directed to a method of enhancing the ability of a human immunodeficiency virus 1 (HIV-1) to transduce a quiescent (G0) cell comprising contacting the cell with a chimeric HIV-1 comprising a lentiviral Vpx protein and maintaining the cell under conditions in which nucleic acid of the chimeric HIV-1 is transferred to the cell, thereby transducing the quiescent cell.

As used herein, a quiescent ($G_0$) cell is a non-dividing cell. An example of a quiescent cell is a monocyte.

EXEMPLIFICATION

Experimental Procedures

Plasmids

The retroviral delivery vector pLEGFP-C1 contains MLV-derived retroviral elements along with a CMV promoter-driven EGFP gene (Clontech; Mountain View, Calif.). Pseudotyping MLV and HIV-1 with VSV-G envelope involved cotransfection with a VSV-G expression plasmid, pMD-G (Naldini et al., 1996). pNL4-3.GFP contains the HIV-1 molecular clone NL4-3 with GFP in place of nef. pNL4-3.Luc plasmid contains luciferase reporter gene in place of envelope. The EGFP cassette in the expression vector pLEGFP-C1 was swapped with dsRed to obtain MLV with dsRed reporter expression (pLdsRed). The SIV clones were derived from $SIV_{PBJ}$ (Fletcher et al., 1996). pMLV-Gagp6 was generated by replacing the RFP cassette in pMLV-Gag-RFP (Addgene plasmid 1814 obtained from Dr. W. Mothes [Sherer et al., 2003]) with p6 amplified from SIVsmm. The Vpx expression vector has been described previously (Sharova et al., 2008).

Cells and Viruses

Human monocytes were obtained from healthy donors by countercurrent centrifugal elutriation (Gendelman et al., 1988). 293T and HeLa cells were maintained in DMEM containing 10% FBS. Pseudotyped MLV (MLV-G) stocks were obtained by transfecting retroviral-packaging 293A cells with pLEGFP-C1 and pMD-G. Virus particles in culture supernatants were harvested after 24 and 48 hr, passed through 0.45 μm filter, and concentrated by ultracentrifugation. Vpx was packaged in MLV by cotransfecting 293A cells with pMD-G, pLdsRed, pMLV-Gagp6, and Vpx expression vectors. Control virus was made with the same plasmids, excluding MLV-Gagp6. Similarly, VSV-G-pseudotyped HIV-1 (HIV-G) was prepared by transfecting 293T cells with pNL4-3. GFP and pMD-G. The viruses were titered by transducing HeLa or TZM-b1 cells with increasing virus inputs followed by flow cytometry analysis of $GFP^+$ cells.

One tissue culture infectious $dose_{50}$ ($TCID_{50}$) is the amount of transfected culture supernatant that generated ~50% $GFP^+$ HeLa cells after 48 hr postinfection. Pseudotyped SIVsmm viruses were obtained by transfecting 293T cells with a PBj 1.9 molecular clone with ($SIV_{WT}$) or without ($SIV_{\Delta Vpx}$) Vpx (Fletcher et al., 1996) along with pMD-G. All virus stocks were treated with DNaseI (Worthington Biochemical Corporation; Lakewood, N.J.) to remove residual transfection DNA. In all experiments, the SIVsmm-PBj strain has been used, unless specified otherwise.

Infection Assays

HeLa cells as well as macrophages were infected with increasing virus inputs ($TCID_{50}$) of HIV1-G and MLV-G. After 4 hr, cells were washed with fresh medium and incubated at 37° C. for the remainder of the experiment. Preinfection studies were performed by first infecting macrophages with pseudotyped $SIV_{WT}$ or $SIV_{\Delta Vpx}$ variants, and 4 hr later, the cells were infected with MLV-G (four $TCID_{50}$) for another 4 hr before washing cells with fresh medium. After 42-72 hr, the numbers of GFP/dsRed cells were quantitated by flow cytometry.

Analysis of Viral Infection by Quantitative PCR

Infected cells were washed with PBS before harvesting samples for DNA analysis. Total DNA was extracted from infected cells by a DNeasy kit (QIAGEN). Quantitative analysis of MLV cDNA intermediates is as described (Bruce et al., 2005). PCR primers and probes for MLV include primers OJWB45 and OJWB48 for late MLV transcripts, OJWB45 and OJWB46 for 2-LTR cDNA, and MLV prb for cDNA detection (Bruce et al., 2005). PCR conditions for amplification of SIV and HIV-1 cDNAs are as described previously (Sharova et al., 2008). Copy number estimates of cDNA and 2-LTR circles were determined on an ABI Prism 7500 fast machine. Integrants were quantitated by Alu-LTR real-time PCR as described by Brussel and Sonigo (Brussel and Sonigo, 2003). Briefly, PCR was first done for 12 cycles using Alu primers and LTR-specific primer tagged with lambda sequence. The PCR product was then diluted 10-fold and was used as a template for a quantitative nested PCR using lambda primer and an LTR-specific reverse primer. The number of cell equivalents in DNA lysates from HeLa cells, monocytes, macrophages, and heterokaryons was determined by PCR using CCR5-specific primers (Hatzakis et al., 2000). The real-time PCR analysis from each sample was carried out in duplicate wells, and most of the values shown in the figures are averages of independent experiments using macrophages from at least three different donors.

APOBEC3G Analysis

H9 cells, monocytes, or macrophages were washed twice with PBS and incubated with lysis buffer containing 50 mM HEPES (pH 7.4), 125 mM NaCl, 0.2% NP-40, and EDTA-free protease inhibitor cocktail (Roche). Cell lysates were clarified by centrifugation at 14,000 rpm for 30 min at 4° C. (Microfuge 22R, Beckman Coulter). Cleared cell lysates were quantitated (Bio-Rad Protein Assay Kit) and analyzed by Fast Performance Liquid Chromatography (FPLC). For RNase treatment of HMM complexes from H9 cells, cell lysates were incubated with 50 µg/ml RNase A (DNase-free, Roche) at room temperature for 1 hr before analysis by FPLC. FPLC was run on an ÄKTA FPLC using a Superose 6 10/300 GL gel filtration column (GE Healthcare). The running buffer contained 50 mM HEPES (pH 7.4), 125 mM NaCl, 0.1% NP-40, 1 mM DTT, and 10% glycerol. Fraction size was set at 1 ml. Twenty microliters of each fraction was boiled with Laemmli buffer (6× reducing, Boston BioProducts, Inc.; Worcester, Mass.) and loaded onto a 10% SDS-PAGE. Proteins were transferred to nitrocellulose membranes and blotted with rabbit antiAPOBEC3G antibody (courtesy of Dr. Tariq Rana) using a Tropix CDP-Star system (PerkinElmer; Waltham, Mass.).

FACS and Macrophage Immunophenotyping

Expression of CD14, CD71, or GFP/dsRed in monocytes/macrophages was monitored by flow cytometry. Cells were collected from day 0 to day 6 postinfection and washed twice with buffer (PBS containing 0.1% FBS and 2 mM EDTA). The washed cells were incubated with an antibody mixture containing PE-conjugated anti-human CD14 (BD Biosciences) and APC-conjugated anti-human CD71 (BD Biosciences) for 40 min. Cells were rinsed twice with washing buffer and fixed with 1% paraformaldehyde. Fixed cells were analyzed by cell flow cytometry analysis using a FACSCalibur System (BD Biosciences) and analyzed with FlowJo software (Tree Star, Inc.; Ashland, Oreg.). The percentages of infected CD71⁻ monocytes and CD71⁺ macrophages were determined from the percentages of GFP⁺/CD71⁺ or GFP'/CD71' cells, respectively.

Cell Fusion

HeLa-macrophage fusion was achieved using paramyxovirus hemagglutininneuraminidase (FIN) protein and fusion (F) proteins as described (Sharova et al., 2008). Briefly, HeLa cells were transfected with pCAGGS-HN and pCAGGS-F expression vectors encoding FIN and F proteins of NDV. Sixteen hours posttransfection, HeLa cells were stained with 1.7 µM DiO, mixed with macrophages stained with 0.85 µM DiD (Molecular Probes) in a ratio of 1:2, and plated in 100 mm dishes. After overnight incubation, cells were infected with MLV for 40 hr. Cell sorting was performed with a FACSAria flow cytometer using the FACSDiva software (Becton Dickinson). Double-stained cells were sorted, and total DNA was isolated using a DNeasy Blood and Tissue Kit (QIAGEN) and analyzed by real-time PCR assay for late MLV cDNA and 2-LTR circles. HeLa-monocyte fusion was achieved using a GenomeONE-CFEX HVJ Envelope Cell Fusion kit (Cosmo Bio Co., Ltd.; Tokyo). Manufacturer's instructions for fusion in suspension were followed. Briefly, GFP-expressing HeLa were mixed with monocytes (ratio 1:6) and incubated in the presence of HVJ-E suspension (1.25 µl/1×10⁶ cells) on ice for 5 min and subsequently at 37° C. for 15 min. Cells were plated in 100 mm dishes and infected with HIV-1 NL4-3. Luc or $SIV_{WT}$ for 40 hr. Prior to cell sorting, cells were stained with an APO-conjugated antibody to CD14 (BD Biosciences). Heterokaryons were sorted based on GFP and APC double staining HIV-1 NL4-3. Luc infection was measured by quantifying luciferase activity, and $SIV_{WT}$ infection was analyzed by real-time POR assay for late cDNA and 2-LTR circles.

Results

A Dominant Restriction Limits MLV Infection of Macrophages

The majority of studies that have examined obstacles to infection of nondividing cells by gammaretroviruses have been conducted with artificially growth-arrested cell lines. Whether similar blocks exist in natural nondividing cells such as macrophages has not been fully examined. In order to gain further insight into the mechanism underlying the block to macrophage transduction by MLV, the extent of viral cDNA synthesis and the efficiency of viral transduction in primary macrophages was examined. Transduction efficiency of HIV-1 and MLV in primary macrophages was assessed relative to transduction efficiencies in HeLa cells, which are permissive to both HIV-1 and MLV transduction. Macrophages were transduced by HIV-1 at a level comparable to that observed in HeLa cells, as evidenced by the frequency of GFP⁺ cells (FIG. 1A) and levels of viral cDNA synthesis (FIG. 1B). In contrast, transduction of macrophages by MLV was highly inefficient (FIGS. 1A and 1B). Therefore, the primary block to transduction of macrophages by MLV appeared to be at the level of reverse transcription. In agreement with a previous study (Jarrosson-Wuilleme et al., 2006), a low level of transduction (2%-3% GFP⁺) of primary macrophages by MLV was observed. While artificially growth-arrested HeLa cells are refractory to transduction by MLV (Lewis and Emerman, 1994; Roe et al., 1993), the block to infection of those cells by MLV was unrelated to the reverse transcription block in terminally differentiated macrophages (FIG. 1C). Levels of MLV cDNA in aphidicolin-treated HeLa cells were comparable to those in untreated HeLa cells, and nuclear localization of viral cDNA (as indicated by 2-LTR circles that are formed in the nucleus) was also comparable.

However, integration of MLV cDNA was inefficient in aphidicolin-treated HeLa cells (FIG. 1C). Therefore, the block that was observed in an artificially growth-arrested cell line was distinct from the block that occurs in natural nondividing targets of lentivirus infection.

It has been previously shown that macrophages harbor a restriction that antagonizes HIV-1, HIV-2, and SIV at the level of reverse transcription and that the Vpx protein of HIV-2/SIVsmm specifically overcomes this restriction (Sharova et al., 2008). Whether the restriction that antagonizes lentivirus infection of macrophages may also be preventing infection of macrophages by MLV was investigated. A heterokaryon strategy that we previously adopted to demonstrate that Vpx countered a dominant restriction that was specifically expressed in macrophages was used (Sharova et al., 2008). Since HeLa cells are highly permissive to MLV infection, heterokaryons were generated between macrophages and HeLa cells, and the susceptibility of the heterokaryons to MLV infection was assessed. When the fusogenic proteins of Newcastle disease virus (NDV) were expressed in HeLa cells, these cells readily fused with primary macrophages (FIG. 2A). HeLa-macrophage heterokaryons (double-stained cells, as indicated by the gate) were then sorted by FACS (FIG. 2A, left panels). A FACS profile of sorted heterokaryons is shown (FIG. 2A, middle panel). Representative images of double-staining heterokaryons are shown (FIG. 2A, right panels). Presort images show one double-staining heterokaryon and two adjacent nonfused cells (DiO stained only), and one heterokaryon postsort is shown. Because of the lipophilic nature of the dyes, fluorescence concentrates in lipid-rich regions of the cell. The block to MLV infection of macrophages was at the level of reverse transcription (FIGS. 1A-1C). Therefore, the ability of MLV to infect HeLa-macrophage heterokaryons was gauged by the relative levels of late MLV cDNA transcripts and 2-LTR circles, which are formed only after completion of viral reverse transcription. While HeLa cells were permissive to MLV infection, macrophages and HeLa-macrophage heterokaryons were not permissive to MLV infection (FIG. 2A). The ability of Vpx to overcome the block to MLV infection of HeLa-macrophage heterokaryons was next examined. When Vpx was expressed in HeLa cells and those cells were allowed to fuse with macrophages, the resulting heterokaryons were rendered permissive to MLV infection (FIG. 2B, right panels). In contrast, HeLa-macrophage heterokaryons not expressing Vpx remained refractory to MLV infection (FIG. 2B). The expression of Vpx in HeLa cells did not increase their susceptibility to MLV infection (FIG. 2C). Furthermore, the block imparted by aphidicolin treatment of HeLa cells was not released when Vpx was expressed in those cells (FIG. 2C). Collectively, these data indicate that nondividing macrophages harbor a dominant restriction that prevents MLV infection, and Vpx overcomes the restriction. Furthermore, the block to MLV infection of nondividing HeLa cells is distinct from that observed in macrophages and is not overcome by Vpx.

Neutralization of the Macrophage Restriction Confers Permissivity to MLV Infection Whether neutralization of the restriction by Vpx would be sufficient to render macrophages permissive to MLV was next examined. First whether introduction of Vpx into macrophages by wild-type SIV ($SIV_{WT}$) infection would render those macrophages susceptible to subsequent transduction by MLV was examined. Infection of primary macrophages with increasing levels of $SIV_{WT}$ (PBj) led to a dose-dependent increase in the level of MLV transduction based on MLV cDNA synthesis (FIG. 3A). Preinfection of macrophages with a $SIV_{WT}$ but not a Vpx-deleted SIV ($SIV_{\Delta Vpx}$) also resulted in an increased ability of MLV to transduce macrophages, as evidenced by MLV cDNA synthesis (FIGS. 3B and 3C) and expression of GFP from the MLV genome (FIG. 3D). It was previously demonstrated that the restriction to infection of macrophages by lentiviruses can be overcome by Vpx from $SIV_{PBJ}$ and HIV-2 but not Vpr of HIV-1 (Sharova et al., 2008). While Vpx alleles from $SIV_{PBJ}$ and $SIV_{mac239}$ enhanced infection of macrophages by MLV, no significant effect was observed with $SIV_{agm}$ Vpr (FIG. 3C). Vpx also appeared to neutralize the restriction in cells in which it was expressed, since MLV transduction occurred predominantly in macrophages that had also been transduced by SIV (GFP expression, FIG. 3E). dsRed$^+$/GFP$^+$ cells in macrophages infected only with SIV (FIG. 3E) was not observed. Therefore, the presence of double-positive cells was not simply due to bleeding of the GFP signal into the dsRed channel.

Packaging of Vpx within MLV Virions Confers a Lentiviral Phenotype

During lentivirus infection of macrophages, the restriction is neutralized by Vpx proteins that are encapsidated within the virus particle (Sharova et al., 2008). Therefore, whether packaging of Vpx within MLV virions would be sufficient to confer upon MLV a lentiviral phenotype, i.e., the ability to transduce macrophages, was examined. The p6 domain of lentiviral gag proteins contains determinants for encapsidation of Vpr/Vpx proteins (Accola et al., 1999; Pancio and Ratner, 1998; Paxton et al., 1993; Wu et al., 1994). The p6 domain of SIV gag was fused to the C terminus of the MLV gag protein (FIG. 4A). Transfection of an MLV packaging cell line with plasmids expressing chimeric MLV gag-SIV p6 proteins, a Vpx expression vector, and a VSV-G envelope-expression vector resulted in the production of VSV-G-pseudotyped chimeric MLV virions containing Vpx. The presence of the VSV-G envelope bypassed the requirement for the presence of MLV receptor molecules on macrophages. Specific packaging of Vpx into MLV particles containing a chimeric gag p6 domain was confirmed by western blotting (FIG. 4B). In contrast, MLV virions derived from a Vpx-expressing MLV packaging line containing wild-type MLV gag (lacking SIV p6) did not package Vpx proteins (FIG. 4B).

Figure 8B:
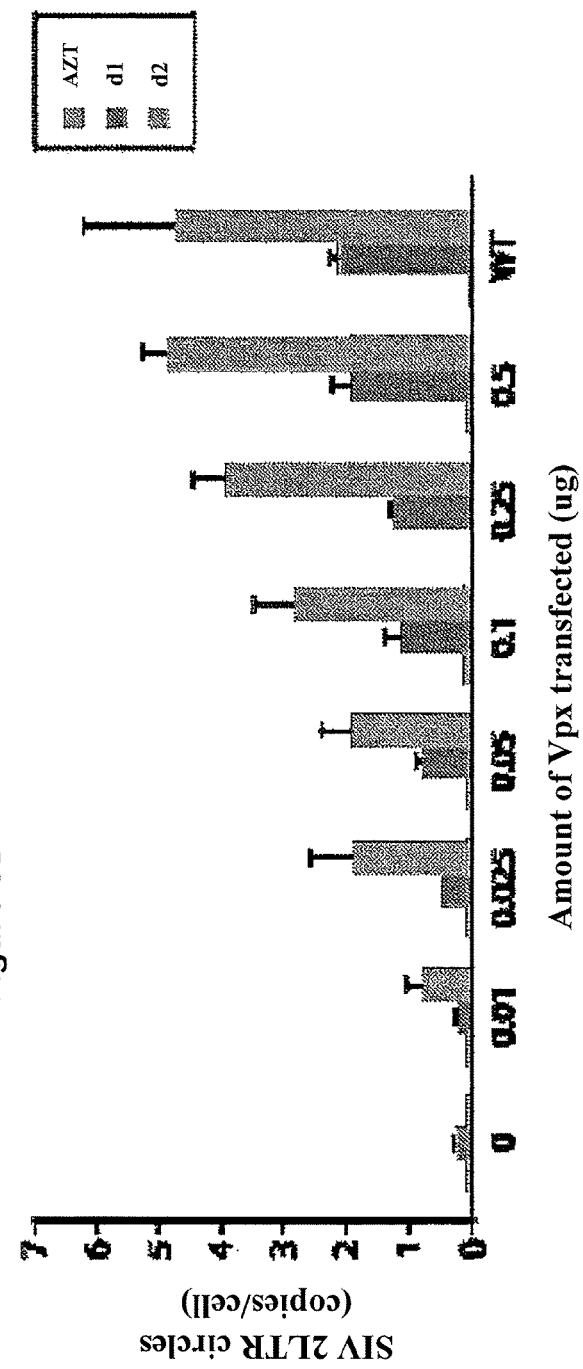

Next examined was the functionality of the p6 domain within the chimeric MLV gag protein by its ability to package a β-lactamase-Vpr fusion protein within virions (Cavrois et al., 2002). Transfer of the β-lactamase-Vpr fusion protein into HeLa cells was then detected by enzymatic cleavage of CCF2, which is a fluorescent substrate of β-lactamase. Infection of CCF2-loaded HeLa cells by chimeric MLV harboring a β-lactamase-Vpr fusion protein resulted in CCF2 cleavage, as evidenced by the appearance of blue cells under fluorescence microscopy (FIG. 4B). This was not the case for CCF2-loaded HeLa cells that had been infected with MLV harboring a wild-type gag protein (FIG. 4B). Packaging of Vpx within MLV virions containing chimeric gag proteins markedly increased their ability to transduce primary macrophages, both in terms of viral cDNA synthesis and integration (FIGS. 4C and 4D) and in terms of red fluorescent protein expression from the MLV genome (FIGS. 4E and 4F). The chimeric MLV variant containing the SIV gag p6 domain required Vpx for infection of macrophages since, in the absence of Vpx, this chimeric MLV did not transduce macrophages (FIG. 4D). Furthermore, MLV cDNA that was detected in these macrophages was synthesized de novo and was inhibited in the presence of AZT (FIG. 4D). Transduction efficiencies of chimeric MLV particles containing Vpx (~15% at high moi) approached those typically observed for lentivirus-based vectors (FIG. 4F, upper panel). The transduction efficiency of MLV with or without packaged Vpx was similar when gauged on HeLa cells (FIG. 4F, lower panel). Collectively, these results indicate that Vpx is sufficient to render primary macrophages permissive to MLV infection and that a restriction is the obstacle to MLV transduction of nondividing macrophages.

The Resistance of Quiescent Monocytes to Lentivirus Transduction Is Governed by a Restriction Circulating peripheral blood monocytes are highly refractory to lentivirus infection in vitro, and infection is blocked at an early postentry step (Collman et al., 1989; Naif et al., 1998; Neil et al., 2001; Rich et al., 1992; Sonza et al., 1996; Triques and Stevenson, 2004). Susceptibility to infection occurs only upon differentiation of monocytes to macrophages (Munk et al., 2002; Sonza et al., 1996; Triques and Stevenson, 2004). First whether the fusion of HeLa cells with monocytes would result in heterokaryons permissive to HIV-1 infection was investigated. To generate HeLa-monocyte heterokaryons, the fusogenic properties of Sendai virus (hemagglutinating virus of Japan [HVJ]) envelope proteins were exploited. The susceptibility of those heterokaryons to HIV-1 and to SIV infection was then examined. SIV infection was gauged from the level of late cDNAs, and HIV-1 infection was determined by luciferase activity expressed from the HIV-1 genome (values were expressed as percentages of those obtained with HeLa cells). As with unfused monocytes, HeLa-monocyte heterokaryons were highly refractory to transduction by HIV-1 (FIG. 5A). It has previously been demonstrated that Vpx increases monocyte infection by SIV (Wolfrum et al., 2007). In agreement, it was observed that both primary monocytes and HeLa-monocyte heterokaryons were permissive to transduction by SIV (FIG. 5A). To examine whether the ability of SIV to transduce primary monocytes was attributable to Vpx, heterokaryons between monocytes and between HeLa cells that expressed the Vpx protein (FIG. 5B) were generated. In this case, the permissivity of HeLa-monocyte heterokaryons to HIV-1 transduction was increased by Vpx (FIG. 5B), whereas HeLa-monocyte heterokaryons not expressing Vpx remained refractory to HIV-1 transduction (FIG. 5B). Since Vpx does not increase the efficiency of HIV-1 infection in HeLa cells, this result was not due to infection of unfused HeLa cells. Therefore, it was concluded that heterokaryons formed between nonpermissive monocytes and permissive HeLa cells are nonpermissive, due to the presence of a dominant restriction, and that this restriction is overcome by Vpx. The amount of Vpx needed to rescue $SIV_{\Delta Vpx}$ infection in macrophages was titered and it was observed that even a small amount of trans-packaged Vpx can counter the restriction present in macrophages (FIGS. 8A-8B). Vpx is packaged in molar amounts equivalent to gag proteins (Henderson et al., 1988). Assuming ~2000 gag molecules per virion (Arthur et al., 1992) and assuming uniform Vpx:gag stoichiometry in each viral particle, Vpx packaged at ~10% of wild-type levels still rescued a ΔVpx virus (FIGS. 8A-8B), indicating that as few as 20 Vpx molecules can counteract the restriction.

Vpx Renders Primary Monocytes Permissive to HIV-1 Transduction

Figure 9:
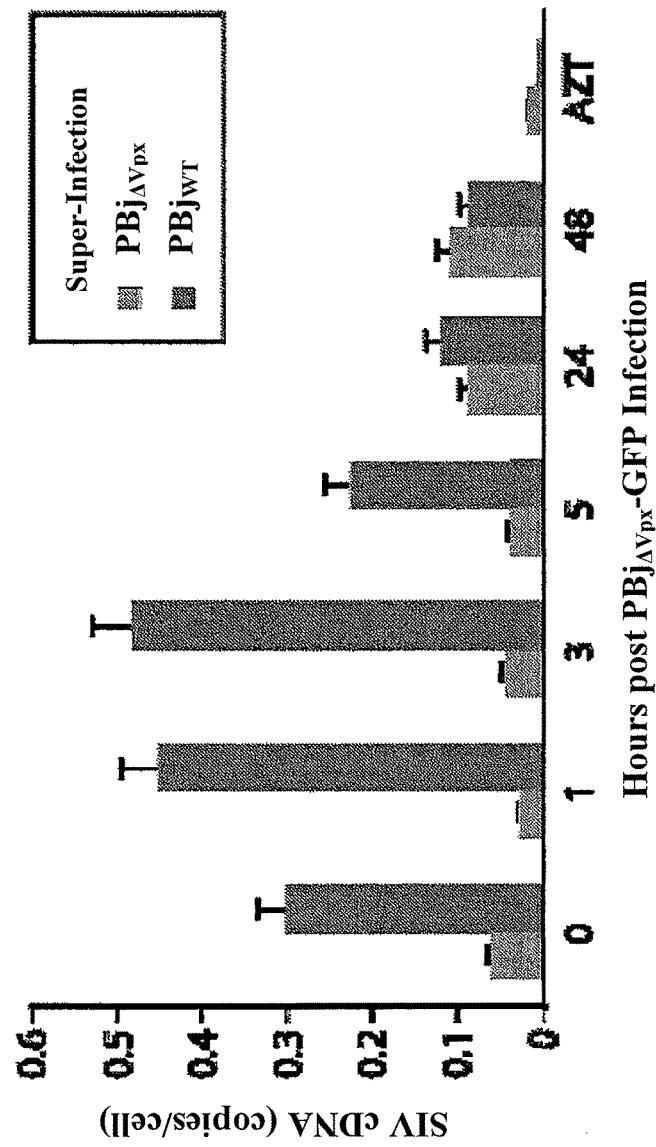
FIG. 9 is a graph showing Reversibility of Restriction. Macrophages were first infected with SIVΔvpx-GFP. After 0, 1, 3, 5, 24, and 48 hr, these cells were superinfected with PBj$_{\Delta Vpx}$, or PBj$_{WT}$ and 24 hr after SIVΔvpx-GFP infection, infection was gauged from quantitation of late viral cDNA using specific primers for the GFP transgene. SIVΔvpx-GFP infection of macrophages in the presence of AZT was used as a control to gauge de novo viral cDNA synthesis. Error bars are SD of replicate samples from two independent experiments done on macrophages from different donors.

Since Vpx was sufficient to render HeLa-monocyte heterokaryons permissive to HIV-1 infection (FIGS. 5A-5B), whether Vpx was sufficient to render monocytes susceptible to HIV-1 transduction was next examined. Since monocytes were partially permissive to $SIV_{WT}$ transduction (FIG. 5A), Vpx was introduced into monocytes by $SIV_{WT}$ infection, and those monocytes were subsequently examined for permissivity to HIV-1. SIV infection rendered monocytes highly permissive to subsequent HIV-1 infection, as evidenced by an increase in HIV-1 cDNA synthesis (FIG. 6A). In contrast, monocytes that had not been preinfected with SIV remained refractory to HIV-1 (FIG. 6A). Furthermore, monocytes infected with $SIV_{WT}$ but not $SIV_{\Delta Vpx}$ could be transduced by HIV-1, as evidenced by expression of GFP from the HIV-1 genome (FIGS. 6B and 6C). Similarly, packaging of Vpx within HIV-1 virions (FIG. 6D) or in an HIV-1 lentivirus vector (pCDH-Vpx) (FIG. 6E) markedly increased the efficiency of transduction in primary monocytes. Also examined was whether the impact of the restriction was reversible. It was speculated that, following infection of macrophages by a $SIV_{\Delta Vpx}$ virus, the infection could be rescued by subsequent introduction of Vpx. At various intervals following infection by a $SIV_{\Delta Vpx}$ virus (containing a GFP transgene), cells were superinfected by $SIV_{WT}$ or $SIV_{\Delta Vpx}$ variants. The ability to rescue the initial $SIV_{\Delta Vpx}$), infection was gauged by PCR using primers specific for GFP. We observed that $SIV_{\Delta Vpx}$ GFP reverse transcription could be restored at least 5 hr later by a wild-type virus (FIG. 9). Since this is in the time frame required for uncoating to occur, it indicates that the restriction might act subsequent to uncoating.

Vpx Affects Monocyte Permissivity Independent of APOBEC3G or Differentiation Status To investigate the possibility that Vpx rendered monocytes permissive to infection by causing a shift in APOBEC3G from LMM to HMM complexes, the distribution of APOBEC3G in uninfected monocytes and in monocytes infected with $SIV_{WT}$ and $SIV_{\Delta Vpx}$ was compared. As published previously (Chiu et al., 2005), APOBEC3G was sequestered primarily in an HMM complex in H9 cells and in differentiated (day 10) macrophages (FIG. 7A). RNase treatment of HMM complexes from H9 cells led to the formation of LMM APOBEC3G complexes (FIG. 7A). In undifferentiated (day 0) monocytes, APOBEC3G was sequestered primarily in an LMM complex (FIG. 7A). Infection of monocytes by $SIV_{WT}$ or $SIV_{\Delta Vpx}$ did not noticeably alter distribution of APOBEC3G between LMM and HMM complexes (FIG. 7A).

It was possible that HIV-1 transduction was restricted to a small percentage of differentiated (CD71$^+$) macrophages in the culture. To examine this, frequencies of infected monocytes (CD71$^-$) and macrophages (CD71$^+$) were examined by FACS following infection with a GFP-expressing HIV-1 variant in which Vpx had been packaged. Infection of monocytes by HIV-1 either with or without Vpx did not have an effect on temporal expression of CD71 (FIG. 7B). In addition, as the frequency of GFP$^+$ cells increased, there was no apparent bias to an increased frequency of CD71$^+$/GFP$^+$ cells (FIG. 7C). Indeed, the frequencies of infected CD71 monocytes at days 2, 3, and 4 postinfection paralleled those for infected CD71$^+$ cells (FIG. 7C). In an independent experiment (FIG. 7D), equivalent transduction of CD71$^+$ and CD71$^-$ by HIV-1 over 6 days postinfection was maintained. Collectively, these results indicate that Vpx directly renders undifferentiated monocytes permissive to HIV-1 transduction without inducing their differentiation.

DISCUSSION

The studies described herein indicate that a cellular restriction is the obstacle to transduction of terminally differentiated macrophages by MLV and that when the restriction is neutralized by the primate lentiviral Vpx protein, macrophages become permissive to MLV. Current models, based primarily on studies with artificially growth-arrested fibroblast cell lines, suggest that the relative abilities of gammaretroviruses and lentiviruses to traverse the nuclear envelope dictate the differential abilities of these viruses to transduce nondividing cells (reviewed in Yamashita and Emerman, 2006). However, it was observed herein that MLV infection of artificially growth-arrested HeLa cells was blocked at the level of integration and not viral cDNA synthesis or nuclear import of viral cDNA. This block was mechanistically distinct from the block we observed in natural nondividing macrophages, where MLV transduction was inhibited either prior to or at the level of reverse transcription of viral cDNA. When the block to reverse transcription in macrophages was alleviated by Vpx, MLV integration and gene expression occurred. Therefore, the differential ability of lentiviruses and gammaretroviruses to transduce nondividing macrophages is dictated by the degree to which they are sensitive to a restriction that acts prior to or at the level of reverse transcription.

Although our studies provide insight into mechanisms that restrict gammaretrovirus infection of nondividing myeloid cells, there still remains the question as to how viral genomes access the nuclear compartment. Packaging of Vpx within MLV particles removed a block to reverse transcription and was sufficient to permit transduction of terminally differentiated macrophages. This indicates that if conditions for viral cDNA synthesis are met, subsequent events including synthesis, nuclear import and integration of viral cDNA, and de novo gene expression occur in nondividing macrophages following both HIV-1 and MLV infection. Therefore, presumably, the ability to traverse the nuclear envelope appears to be an intrinsic property of gammaretroviruses and lentiviruses. Models invoking a nuclear import role for VprNpx proteins have been supported by the fact that these proteins exhibit a nuclear localization (reviewed in Yamashita and Emerman, 2006). While the data provided herein argue against the possibility that nuclear access is blocked during MLV infection of nondividing macrophages, it is possible that the restriction is located in the nucleus and that Vpx must localize to the nucleus in order to counteract the restriction.

It was previously demonstrated (Sharova et al., 2008) that infection of macrophages by HIV-1 is influenced by a restriction and that this restriction is sensitive to neutralization by Vpx, but not SIVsmm Vpr or HIV-1 Vpr. Herein it is demonstrate that Vpx but not Vpr alleles of primate lentiviruses enhance infection of macrophages by MLV. All primate lentiviruses encode a Vpr protein. The Vpx gene of the HIV-2 group, which includes HIV-2, SIVsmm, and $SIV_{mac}$, arose by duplication of the Vpr gene within this group (Sharp et al., 1996; Tristem et al., 1992), which diverged from the other primate lentiviral groups around 200 years ago (Tristem et al., 1992). While Vpx represents a duplication, it does not share all the functional properties of Vpr. Vpr induces cell cycle arrest, whereas Vpx does not (Fletcher et al., 1996). Conversely, the ability to neutralize a restriction in myeloid cells is governed by Vpx but not Vpr. Presumably, this activity was manifest in the ancestral Vpr gene, but for unknown reasons has been lost in the HIV-1 and $SIV_{agm}$ groups. It is possible that loss in the ability to counteract the myeloid cell restriction was compensated for by acquisition of partial resistance to the restriction, as in the case of HIV-1.

The studies herein further implicate a restriction as the obstacle to infection of quiescent monocytes by lentiviruses. It is likely that this same restriction antagonizes HIV-1 infection in monocytes and in macrophages. However, the degree to which HIV-1 is restricted in monocytes and macrophages differs considerably. In the absence of Vpx, HIV-1 still has the ability to transduce macrophages to some degree. Nevertheless, the efficiency with which HIV-1 transduces macrophages is greatly increased by Vpx. Therefore, while infection of macrophages by HIV-1 is antagonized by a restriction, this restriction is not sufficient to completely block transduction of these cells by HIV-1. In contrast, monocytes are totally refractory to HIV-1 infection in the absence of Vpx. Therefore, monocytes can be considered fully nonpermissive and macrophages semipermissive to HIV-1 transduction. The extent to which monocytes and macrophages are permissive to infection may relate to the levels at which the restriction is expressed in these cells. A similar situation is seen with APOBEC3G, in that some cell lines are semipermissive with regards to Vif-deleted virus (Sheehy et al., 2002).

While the restriction that is counteracted by Vpx is as yet unidentified, it exhibits unique characteristics when compared to other known antiviral restrictions. Viral Vif and Vpu proteins that neutralize the antiviral restrictions APOBEC3G and tetherin/BST2, respectively, carry out their function in the virus-producing cell (reviewed in Malim and Emerman, 2008). Although some Vif is packaged within virions, there is no evidence that packaged Vif has a functional role in viral infection. By comparison, the ability of Vpx to neutralize the myeloid cell restriction appears to require that it is packaged within virions. Indeed, Vpx protein that was packaged into virions effected a durable removal of the block to subsequent infection by a restricted virus. This indicates that the restriction has an extremely low turnover rate and takes a considerable time to recover after it has been neutralized by Vpx.

The study described herein underscores the powerful degree to which restrictions shape lentivirus biology. Primate lentiviruses exhibit tropism for macrophage lineage cells, and reservoirs of tissue macrophages are evident in the gut, lung, lymph nodes, and CNS (reviewed in Gonzalez-Scarano and Martin-Garcia, 2005). Tropism is dictated primarily by the expression of specific coreceptor molecules (mainly CCR5) on macrophages that permit virus binding and entry (reviewed in Gorry et al, 2005). The study herein reveals a second level of tropism that is manifest postentry, and these findings indicate that the ability of primate lentiviruses and likely nonprimate lentiviruses as well to establish reservoirs in myeloid lineage cells is dependent upon their ability to counteract a myeloid cell-specific restriction. Given the potency with which the restriction antagonizes primate lentivirus infection, identification of the restriction itself as well as pharmacologic agents that harness restrictions within macrophages are important objectives.

REFERENCES

Accola, M. A., Bukovsky, A. A., Jones, M. S., and Gbttlinger, H. G. (1999). A conserved dileucine-containing motif in p6(gag) governs the particle associ⁻ ation of Vpx and Vpr of simian immunodeficiency viruses SIV(mac) and SIV (agm). J. Virol, 73, 9992-9999.

Arthur, L. O., Bess, J. W., Snowder, R. C., II, Benveniste, R. E., Mann, D. L., Chermann, J.-C., and Henderson, L. E. (1992). Cellular proteins bound to immunodeficiency viruses: implications for pathogenesis and vaccines. Science 258, 1935-1938.

Balliet, J. W., Kolson, D. L., Eiger, G., Kim, F. M., McGann, K. A., Srinivasan, A., and Collman, R. (1994). Distinct effects in primary macrophages and lympho⁻ cytes of the human immunodeficiency virus type 1 accessory genes vpr, vpu, and nef: mutational analysis of a primary HIV-1 isolate, Virology 200, 623-631.

Bieniasz, P. D., Weiss, R. A., and McClure, M. O. (1995). Cell cycle dependence of foamy retrovirus infection. J. Virol. 69, 7295-7299.

Bowerman, B., Brown, P. O., Bishop, J. M., and Varmus, H. E. (1989). A nucle⁻ oprotein complex mediates the integration of retroviral DNA. Gend. Dev. 3, 469-478.

Bruce, J. W., Bradley, K. A., Ahlquist, P., and Young, J. A. (2005). Isolation of cell lines that show novel, murine leukemia virus-specific blocks to early steps of retroviral replication. J. Virol. 79, 12969-12978.

Brussel, A., and Sonigo, P. (2003). Analysis of early human immunodeficiency virus type 1 DNA synthesis by use of a new sensitive assay for quantifying inte⁻ grated provirus. J. Virol. 77, 10119-10124.

Bukrinsky, M. I., Sharova, N., Dempsey, M. P., Stanwick, T. L., Bukrinskaya, A. G., Haggerty, S., and Stevenson, M. (1992). Active nuclear import of human immunodeficiency virus type 1 preintegration complexes. Proc. Natl. Acad. Sci. USA 89, 6580-6584.

Cavrois, M., De Noronha, C., and Greene, W. C. (2002). A sensitive and specific enzyme-based assay detecting HIV-1 virion fusion in primary T lymphocytes. Nat. Biotechnol. 20, 1151-1154.

Chiu, Y. L., Soros, V. B., Kreisberg, J. F., Stopak, K., Yonemoto, W., and Greene, W. C. (2005). Cellular APOBEC3G restricts HIV-1 infection in resting CD4+ T cells. Nature 435, 108-114.

Coltman, R., Hassan, N. F., Walker, R., Godfrey, B., Cutilli, J, Hastings, J. C., Friedman, H., Douglas, S. D., and Nathanson, N. (1989). Infection of mono⁻ cyte-derived macrophages with human immunodeficiency virus type 1 (HIV-1). Monocyte-tropic and lymphocyte-tropic strains of HIV-1 show distinctive patterns of replication in a panel of cell types. J. Exp. Med. 170, 1149-1163.

Connor, R. I., Chen, B. K., Choe, S., and Landau, N. R. (1995). Vpr is required for efficient replication of human immunodeficiency virus type-1 in mononuclear phagocytes. Virology 206, 935-944, Di Marzio, P., Tse, J., and Landau, N. R. (1998). Chemokine receptor regulation and HIV type 1 tropism in monocyte-macrophages. AIDS Res. Hum. Retroviruses 14, 129-138.

Eisert, V., Kreutz, M., Becker, K., Königs, C., Alex, U., RObsamen-Waigmann, H., Andreesen, R., and von Briesen, H. (2001). Analysis of cellular factors influencing the replication of human immunodeficiency virus type I in human macrophages derived from blood of different healthy donors. Virology 286, 31-44.

Ellery, P. J., Tippett, E., Chiu, Y. L., Paukovics, G., Cameron, P. U., Solomon, A., Lewin, S. R., Gorry, P. R., Jaworowski, A., Greene, W. C., et al. (2007). The CD16+ monocyte subset is more permissive to infection and preferentially harbors HIV-1 in vivo. J. Immunol. 178, 6581-6589.

Fletcher, T. M., 3rd, Brichacek, B., Sharova, N., Newman, M. A., Stivahtis, G., Sharp, P. M., Emerman, M., Hahn, B. H., and Stevenson, M. (1996). Nuclear import and cell cycle arrest functions of the HIV-1 Vpr protein are encoded by two separate genes in HIV-2/SIM(SM). EMBO J. 15, 6155-6165.

Gartner, S., Markovits, P., Markovitz, D. M., Kaplan, M. H., Gallo, R. C., and Popovic, M. (1986). The role of mononuclear phagocytes in HTLV-III/LAV infection. Science 233, 215-219.

Gendelman, H. E., Orenstein, J. M., Martin, MA, Ferruca, C., Mitre, R., Phipps, T., Wahl, L. A., Lane, H. C., Fauci, A. S., and Burke, D. S. (1988). Efficient isolation and propagation of human immunodeficiency virus on recombinant colony-stimulating factor 1-treated monocytes. J. Exp. Med. 167, 1428-1441.

Gonzalez-Scarano, F., and Martin-Garcia, J. (2005). The neuropathogenesis of AIDS. Nat. Rev. Immunol. 5, 69-81.

Gorry, P. R., Churchill, M., Crowe, S. M., Cunningham, A. L., and Gabuzda, D. (2005). Pathogenesis of macrophage tropic HIV-1. Curr. HIV Res, 3, 53-60.

Goujon, C., Arfi, V., Pertel, T., Luban, J., Lienard, J., Rigal, D., Darlix, J. L., and Cimarelli, A. (2008). Characterization of simian immunodeficiency virus SIVSM/human immunodeficiency virus type 2 Vpx function in human myeloid cells. J. Virol. 82, 12335-12345.

Hatzakis, A., Touloumi, G., Karanicolas, R., Karafoulidou, A., Mandalaki, T., Anastassopoulou, C., Zhang, L., Goedert, J. J., Ho, D. D., and Kostrikis, L. G. (2000). Effect of recent thymic emigrants on progression of HIV-1 disease. Lancet 355, 599-604.

Heinzinger, N., Bukrinsky, M., Haggerty, S., Ragland, A., Lee, M.-A., Kewalramani, V., Gendelman, H., Ratner, L., Stevenson, M., and Emerman, M. (1994). The Vpr protein of human immunodeficiency virus type 1 influences nuclear localization of viral nucleic acids in nondividing host cells. Proc. Natl. Acad. Sci. USA 91, 7311-7315.

Henderson, L. E., Sowder, R. C., Copeland, T. D., Benveniste, R. E., and Oroszlan, S. (1988). Isolation and characterization of a novel protein (X-ORF product) from SIV and HIV-2. Science 241, 199-201.

Jarrosson-Wuilleme, L., Goujon, C., Bernaud, J., Rigal, D., Darlix, J. L., and Cimarelli, A. (2006). Transduction of nondividing human macrophages with gammaretrovirus-derived vectors. J. Virol. 80, 1152-1159.

Lewis, P., Hensel, M., and Emerman, M. (1992). Human immunodeficiency virus infection of cells arrested in the cell cycle. EMBO J. 11, 3053-3058.

Lewis, P. F., and Emerman, M. (1994). Passage through mitosis is required for oncoretroviruses but not for the human immunodeficiency virus. J. Virol. 68, 510-516.

Malim, M. H., and Emerman, M. (2008). HIV-1 accessory proteins-ensuring viral survival in a hostile environment. Cell Host Microbe 3, 388-398.

Münk, C., Brandt, S. M., Lucero, G., and Landau, N. R. (2002). A dominant block to HIV-1 replication at reverse transcription in simian cells. Proc. Natl. Acad. Sci. USA 99, 13843-13848.

Naif, H. M., Li, S., Alall, M., Sloane, A., Wu, L., Kelly, M., Lynch, G., Lloyd, A., and Cunningham, A. L. (1998). CCR5 expression correlates with susceptibility of maturing monocytes to human immunodeficiency virus type 1 infection. J. Virol. 72, 830-836.

Naldini, L., Blamer, U., Gallay, P., Ory, D., Mulligan, R., Gage, F. H., Verma, I. M., and Trono, D. (1996). In vivo gene delivery and stable transduction of nondividing cells by a lentiviral vector. Science 272, 263-267.

Neil, S., Martin, F., Ikeda, Y., and Collins, M. (2001). Postentry restriction to human immunodeficiency virus-based vector transduction in human monocytes. Virol. 75, 5448-5456.

O'Brien, W A., Namazi, A., Kalhor, H., Mae, S.-H., Zack, J. A., and Chen, I. S. (1994). Kinetics of human immunodeficiency virus type 1 reverse transcription in blood mononuclear phagocytes are slowed by limitations of nucleotide precursors. J. Virol. 68, 1258-1263.

Pancio, H. A., and Ratner, L. (1998). Human immunodeficiency virus type 2 Vpx-Gag interaction. J. Virol. 72, 5271-5275.

Paxton, W., Connor, R. I., and Landau, N. R. (1993). Incorporation of Vpr into human immunodeficiency virus type 1 virions: requirement for the p6 region of gag and mutational analysis. J. Virol. 67, 7229-7237.

Peng, G., Lei, K. J., J M, W., Greenwell-Wild, T., and Wahl, S. M. (2006). Induction of APOBEC3 family proteins, a defensive maneuver underlying interferon-induced anti-HIV-1 activity. J. Exp. Med. 203, 41-46.

Peng, G., Greenwell-Wild, T., Nares, S., Jin, W., Lei, K. J., Rangel, Z. G., Munson, P. J., and Wahl, S. M. (2007). Myeloid differentiation and susceptibility to HIV-1 are linked to APOBEC3 expression. Blood 110, 393-400.

Rich, E A., Chen, I. S., Zack, J. A., Leonard, M. L., and O'Brien, W. A. (1992). Increased susceptibility of differentiated mononuclear phagocytes to productive infection with human immunodeficiency virus-1 (HIV-1). Clin. Invest. 89, 176-183.

Ringler, D. J., Wyand, M. S., Walsh, D. G., MacKey, J. J., Chalifoux, L. V., Popovic, M., Minassian, A. A., Sehgal, P. K., Daniel, M. D., Desrosiers, R. C., et al. (1989). Cellular localization of simian immunodeficiency virus in lymphoid tissues. I. Immunohistochemistry and electron microscopy. Am. J. Pathol. 134, 373-383.

Roe, T., Reynolds, T. C., Yu, G., and Brown, P. O. (1993). Integration of murine leukemia virus DNA depends on mitosis. EMBO J. 12, 2099-2108.

Sharova, N., Wu, Y., Zhu, X., Stranska, R., Kaushik, R., Sharkey, M., and Stevenson, M. S. (2008). Primate lentiviral Vpx commandeers DDB1 to counteract a macrophage restriction. PLoS Pathog. 4, e1000057.

Sharp, P. M., Bailes, E., Stevenson, M., Emerman, M., and Hahn, B. H. (1996). Gene acquisition in HIV and SIV. Nature 383, 586-587.

Sheehy, A. M., Gaddis, N. C., Choi, J. D., and Malim, M. H. (2002). Isolation of a human gene that inhibits HIV-1 infection and is suppressed by the viral Vif protein. Nature 418, 646-650.

Sherer, N. M., Lehmann, M. J., Jimenez-Soto, L. F., Ingmundson, A., Horner, S. M., Cicchetti, G., Allen, P. G., Pypaert, M., Cunningham, J. M., and Mothes, W. (2003). Visualization of retroviral replication in living cells reveals budding into multivesicular bodies. Traffic 4, 785-801.

Sonza, S., Maerz, A., Deacon, N., Meanger, J., Mills, J., and Crowe, S. (1996). Human immunodeficiency virus type 1 replication is blocked prior to reverse transcription and integration in freshly isolated peripheral blood monocytes. J. Virol. 70, 3863-3869.

Srivastava, S., Swanson, S. K., Manel, N., Florens, L., Washburn, M. P., and Skowronski, J. (2008). Lentiviral Vpx accessory factor targets VprBP/DCAF1 substrate adaptor for cullin 4 E3 ubiquitin ligase to enable macrophage infection. PLoS Pathog. 4, e1000059.

Suzuki, Y., and Craigie, R. (2007). The road to chromatin—nuclear entry of retroviruses. Nat. Rev. Microbiol. 5, 187-196.

Triques, K., and Stevenson, M. (2004). Characterization of restrictions to human immunodeficiency virus type 1 infection of monocytes. J. Virol. 78, 5523-5527.

Tristem, M., Marshall, C., Karpas. A., and Hill, F. (1992). Evolution of the primate lentiviruses: evidence from vpx and vpr. EMBO J. 11, 3405-3412.

Weinberg, J. B., Matthews, T. J., Cullen, B. R., and Malim, M. N. (1991). Productive human immunodeficiency virus type 1 (HIV-1) infection of nonproliferating human monocytes. J. Exp. Med. 174, 1477-1482.

Wolfrum, N., MOhlebach, M. D., SchOle, S., Kaiser, J. K., Kloke, B. P., Cichutek, K., and Schweizer, M. (2007). Impact of viral accessory proteins of SIVsmmPBj on early steps of infection of quiescent cells. Virology 364, 330-341.

Wu, X., Conway, J. A., Kim, J., and Kappes, J. C. (1994). Localization of the Vpx packaging signal within the C terminus of the human immunodeficiency virus type 2 gag precursor protein. J. Virol. 68, 6161-6169.

Yamashita, M., and Emerman, M. (2006). Retroviral infection of non-dividing cells: old and new perspectives. Virology 344, 88-93.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A method of transducing a non-dividing myeloid cell comprising contacting the cell with a chimeric murine leukemia virus (MLV) comprising an MLV virion which contains a lentiviral Vpx protein and maintaining the cell under conditions in which nucleic acid of the chimeric MLV is transferred to the cell, thereby transducing the non-dividing myeloid cell.

2. The method of claim 1 wherein the chimeric MLV further comprises an exogenous sequence that is expressed upon transduction of the chimeric MLV into the non-dividing myeloid cell.

3. A method of enhancing the ability of a murine leukemia virus (MLV) to transduce a non-dividing myeloid cell comprising contacting the cell with a chimeric MLV comprising an MLV virion which contains a lentiviral Vpx protein and maintaining the cell under conditions in which nucleic acid of the chimeric MLV is transferred to the cell, thereby enhancing the ability of a MLV to transduce the non-dividing myeloid cell.

4. The method of claim 3 wherein the chimeric MLV further comprises an exogenous sequence that is expressed upon transduction of the chimeric MLV into the non-dividing myeloid cell.

5. The method of claim 1 wherein the lentiviral Vpx protein is a primate lentiviral Vpx protein.

6. The method of claim 5 wherein the primate lentiviral Vpx protein is a Simian Immunodeficiency Virus (SIV) Vpx protein.

7. The method of claim 6 wherein the SIV Vpx protein is fused to a C terminus of a MLV gag protein.

8. The method of claim 7 further comprising all or a portion of a SIV gag protein fused to the C terminus of the MLV gag protein.

9. The method of claim 8 wherein the portion of the SIV gag protein is a p6 domain.

10. The method of claim 6 wherein the SIV Vpx has an amino acid sequence comprising:
MSXPRERIPP GNSGEETXGE AFDWLHRTXE EINRAAVNHL PRELIFQVWR RXWEYWHDEM GMSVSYTKXR YLCLIQKALF MHCKKGCRCL GGEHGAGGWR PGPPPPPPG LA (SEQ ID NO: 1);
or
MSDPRERIPP GNSGEETIGE AFDWLHRTVE EINRAAVNHL PRELIFQVWR RSWEYWHDEM GMSVSYTKYR YLCLIQKAMF MHCKKGCRCL GGEHGAGGWR PGPPPPPPG LA (SEQ ID NO: 2).

11. The method of claim 7 wherein the MLV gag protein has an amino acid sequence comprising (SEQ ID NO: 3)
MFIPLIFLPQLLGNVLVCVLAHHFGKEFMGQTVTTPLSLTLGHWKDVE
RIAHNQSVDVKKRRWVTFCSAEWPTFNVGWPRDGTFNRDLITQVKIKV
FSPGPHGHPDQVPYIVTWEALAFDPPPWVKPFVHPKPPPPLPPSAPSL
PLEPPRSTPPRSSLYPALTPSLGAKPKPQVLSDSGGPLIDLLTEDPPP
YRDPRPPPSDRDGNGGEATPAGEAPDPSPMASRLRGRREPPVADSTTS
QAFPLRAGGNGQLQYWPFSSSDLYNWKNNNPSFSEDPGKLTALIESVL
ITHQPTWDDCQQLLGTLLTGEEKQRVLLEARKAVRGDDGRPTQLPNEV
DAAFPLERPDWDYTTQAGRNHLVHYRQLLLAGLQNAGRSPTNLAKVKG
ITQGPNESPSAFLERLKEAYRRYTPYDPEDPGQETNVSMSFIWQSAPD
IGRKLERLEDLKNKTLGDLVREAEKIFNKRETPEEREERIRRETEEKE
ERRRTEDEQKEKERDRRRHREMSKLLATVVSGQKQDRQGGERRRSQLD
RDQCAYCKEKGHWAKDCPKKPRGPRGPRPQPVATMASSEDVIKEFMRF
KVRMEGSVNGHEFEIEGEGEGRPYEGTQTAKLKVTKGGPLPFAWDILS
PQFQYGSKAYVKHPADIPDYLKLSFPEGFKWERVMNFEDGGVVTVTQD
SSLQDGEFIYKVKLRGTNFPSDGPVMQKKTMGWEASTERMYPEDGALK
GEIKMRLKLKDGGHYDAEVKTTYMAKKPVQLPGAYKTDIKLDITSHNE
DYTIVEQYERAEGRHSTGALYK.

12. The method of claim 1 wherein the non-dividing myeloid cell is a terminally differentiated cell.

13. The method of claim 12 wherein the terminally differentiated cell is selected from the group consisting of: a macrophage, a dendritic cell.

14. The method of claim 3 wherein the lentiviral Vpx protein is a primate lentiviral Vpx protein.

15. The method of claim 14 wherein the primate lentiviral Vpx protein is a Simian Immunodeficiency Virus (SIV) Vpx protein.

16. The method of claim 15 wherein the SIV Vpx protein is fused to a C terminus of a MLV gag protein.

17. The method of claim 16 further comprising all or a portion of a SIV gag protein fused to the C terminus of the MLV gag protein.

18. The method of claim 17 wherein the portion of the SIV gag protein is a p6 domain.

19. The method of claim 15 wherein the SIV Vpx has an amino acid sequence comprising:
MSXPRERIPP GNSGEETXGE AFDWLHRTXE EINRAAVNHL PRELIFQVWR RXWEYWHDEM GMSVSYTKXR YLCLIQKALF MHCKKGCRCL GGEHGAGGWR PGPPPPPPG LA (SEQ ID NO: 1);
or
MSDPRERIPP GNSGEETIGE AFDWLHRTVE EINRAAVNHL PRELIFQVWR RSWEYWHDEM GMSVSYTKYR YLCLIQKAMF MHCKKGCRCL GGEHGAGGWR PGPPPPPPG LA (SEQ ID NO: 2).

20. The method of claim 16 wherein the MLV gag protein has an amino acid sequence comprising (SEQ ID NO: 3)
MFIPLIFLPQLLGNVLVCVLAHHFGKEFMGQTVTTPLSLTLGHWKDVE
RIAHNQSVDVKKRRWVTFCSAEWPTFNVGWPRDGTFNRDLITQVKIKV
FSPGPHGHPDQVPYIVTWEALAFDPPPWVKPFVHPKPPPPLPPSAPSL
PLEPPRSTPPRSSLYPALTPSLGAKPKPQVLSDSGGPLIDLLTEDPPP
YRDPRPPPSDRDGNGGEATPAGEAPDPSPMASRLRGRREPPVADSTTS
QAFPLRAGGNGQLQYWPFSSSDLYNWKNNNPSFSEDPGKLTALIESVL
ITHQPTWDDCQQLLGTLLTGEEKQRVLLEARKAVRGDDGRPTQLPNEV
DAAFPLERPDWDYTTQAGRNHLVHYRQLLLAGLQNAGRSPTNLAKVKG
ITQGPNESPSAFLERLKEAYRRYTPYDPEDPGQETNVSMSFIWQSAPD
IGRKLERLEDLKNKTLGDLVREAEKIFNKRETPEEREERIRRETEEKE
ERRRTEDEQKEKERDRRRHREMSKLLATVVSGQKQDRQGGERRRSQLD
RDQCAYCKEKGHWAKDCPKKPRGPRGPRPQPVATMASSEDVIKEFMRF -continued

```
KVRMEGSVNGHEFEIEGEGEGRPYEGTQTAKLKVTKGGPLPFAWDILS

PQFQYGSKAYVKHPADIPDYLKLSFPEGFKWERVMNFEDGGVVTVTQD

SSLQDGEFIYKVKLRGTNFPSDGPVMQKKTMGWEASTERMYPEDGALK

GEIKMRLKLKDGGHYDAEVKTTYMAKKPVQLPGAYKTDIKLDITSHNE

DYTIVEQYERAEGRHSTGALYK.
```

21. The method of claim 3 wherein the non-dividing myeloid cell is a terminally differentiated cell.

22. The method of claim 21 wherein the terminally differentiated cell selected from the group consisting of: a macrophage, a dendritic cell.

* * * * *